(12) United States Patent
Hurlburt et al.

(10) Patent No.: US 6,699,662 B1
(45) Date of Patent: Mar. 2, 2004

(54) INHIBITORS OF STAPHYLOCOCCUS SARA PROTEIN FUNCTION INVOLVED IN THE EXPRESSION OF STAPHYLOCOCCAL VIRULENCE FACTORS AND THE USE THEREOF IN TREATING STAPHYLOCOCCAL INFECTIONS

(75) Inventors: Barry K. Hurlburt, Little Rock, AR (US); Mark S. Smeltzer, Bryant, AR (US); Tammy M. Rechtin, Homewood, AL (US)

(73) Assignee: University of Arkansas, Little Rock, AR (US)

( * ) Notice: Subject to any disclaimer, the term of this patent is extended or adjusted under 35 U.S.C. 154(b) by 0 days.

(21) Appl. No.: 09/612,549

(22) Filed: Jul. 7, 2000

Related U.S. Application Data
(60) Provisional application No. 60/142,793, filed on Jul. 8, 1999.

(51) Int. Cl.[7] ............................ C12Q 1/68; C12P 19/34; C07H 21/62
(52) U.S. Cl. ................. 435/6; 435/91.2; 536/23.1; 536/24.1; 536/24.5
(58) Field of Search .................. 435/6, 91.2; 536/23.1, 536/24.5, 24.1

(56) References Cited

FOREIGN PATENT DOCUMENTS

| WO | 97/11690 | 4/1997 |
|---|---|---|
| WO | 98/35702 | 8/1998 |

OTHER PUBLICATIONS

Chien et al, "Molecular interactions between two global regulators, sar and agr, in *Staphlococcus aureus*", J. Biol. Chem. (1998) 273(5):2645–2652.*

Novick et al, "The agr P2 operon: an autocatalytic sensory transduction system in *Staphlococcus aureus*", Mol. Gen. Genetics (1995) 248:446–458.*

A. Abdelnour et al., "The Accessory Gene Regulator (agr) Controls . . . Murine Arthritis Model", Infection and Immunity, vol. 61, No. 9, pp. 3879–3885, Sep. 1993, Am. Soc. for Microbiology.

N. Balaban et al., "Autoinducer of Virulence As a Target for Vaccine and Therapy Against *Staphylococcus aureus*", vol. 280, pp. 438–440, Apr. 17, 1998.

M. C. Booth et al. "Accessory Gene Regulator Controls *Staphylococcus aureus* Virulence in Endophthalmitis", Investigative Ophthal. & Visual Sci., vol. 36, No. 9, Aug. 1995, Assoc. for Research in Vision and Ophthal.

A.L. Cheung et al., "Role of the *sar* Locus of *Staphylococcus aureus* in Induction of Endocarditis in Rabbits", Infection and Immunity, vol. 62, No. 5, pp. 1719–1725, May 1994, Am. Society for Microbiology.

A.L. Cheung et al., Diminished Virulence of a sar⁻/agr⁻ Mutant of . . . Model of Endocarditis, Journal of Clinical Investigation, Inc., vol. 94, pp. 1815–1822, Nov. 1994.

A.L. Cheung et al., "sar Genetic Determinants Necessary for Transcription of RNAII and RNAIII in the agr Locus of *Staphylococcus aureus*", J. Bacteriology, pp. 3963–3971, Jun. 1997, (XP–002155701).

Y.T. Chien et al., "Molecular Interactions between Two Global Regulators, sar and agr, in *Staphylococcus Aureus*", J. Biol. Chem., vol. 273:5, pp. 2645–2652, Jan. 1998, (XP–002155700),.

Y.T. Chien et al., "SarA, a Global Regulator of Virulence Determinants . . . Gene Regulation", J. Biol. Chem., vol. 274:52, pp. 37169–37176, Dec. 1999 (XP–002155703).

A.F. Gillaspy et al., "Role of accessory Gene Regulator (agr) in Pathogenesis of Staphylococcal Osteomyelitis" Infection and Immunity, vol. 63, No. 9, pp. 3373–3380, Sep. 1995, Am. Soc. of Microbiology.

L. Good et al., "Antisense inhibition of gene expression in bacteria by PNA targeted to mRNA", JRE Biotechnology, vol. 16, pp. 355–358, Apr. 1998.

G. Ji et al., "Bacterial Interference Caused by Autoinducing Peptide Variants" Science, vol. 276, pp. 2027–2030, Jun. 27, 1997.

S.J. Maleki et al., "MyoD–E12 Heterodimera and MyoD–MyoD Homodimers are Equally Stable", Biochem., vol. 36:22, pp. 6762–6767, 1997.

E. Morfeldt et al., "Transcriptional control of a *agr*–dependent virulence gene . . . in *Staphylococcus aureus*", Molecular Microbiology, vol. 21, No. 6, pp. 1227–1237, 1996, Blackwell Science Ltd.

T.M. Rechtin et al., "Characterization of the SarA virulence gene regulator of *Staphylococcus aureus*", Mol. Microbiology, vol. 33:2, pp. 307–316, 1999, Blackwell Science Ltd.

* cited by examiner

*Primary Examiner*—Jeffrey Fredman
(74) *Attorney, Agent, or Firm*—Foley & Lardner

(57) ABSTRACT

The present invention relates to inhibitors of Staphylococcus SarA protein function involved in the expression of staphylococcal virulence factors and the use of these inhibitors to treat and prevent staphylococcal infections in subjects. Particularly, the inhibitors act to interfere with the binding of the SarA protein to its binding site(s). The selection of specific inhibitors of the SarA protein is made possible as a result of the identification of the binding sites of SarA protein on at least a portion of the agr (accessory gene regulator) gene, a gene that like the sar (staphylococcal accessory regulator) gene, plays a role in the virulence of Staphylococcus. The present invention also is directed to a method of designing, synthesizing and identifying inhibitors of Sar A function and its role in the expression of staphylococcal virulence factors.

25 Claims, 15 Drawing Sheets

A

B

B
```
A1        -------ATTTTCCAATTTTTCTTA
C2        --CTGTCATTATACGATTTAG----
A2        --TAAGAATAAAAAACGAC------
C1        CAATATAATGATAAAAGAT------
B1        ----TTAAATACAAATTACAT----
B2        -----GAAATAAATACTTAACT--- con       -------ATTATAAAATWT------
```

INHIBITORS OF STAPHYLOCOCCUS SARA PROTEIN FUNCTION INVOLVED IN THE EXPRESSION OF STAPHYLOCOCCAL VIRULENCE FACTORS AND THE USE THEREOF IN TREATING STAPHYLOCOCCAL INFECTIONS

RELATED APPLICATIONS

This application is a continuation-in-part of U.S. Serial No. 60/142,793 filed on Jul. 8, 1999, and which is incorporated in its entirety by reference.

BACKGROUND OF THE INVENTION

1. Field of the Invention

The present invention relates to inhibitors of Staphylococcus SarA protein function involved in the expression of staphylococcal virulence factors and the use of these inhibitors to treat and prevent staphylococcal infections in subjects. Particularly, the inhibitors act to interfere with the binding of the SarA protein to its binding site(s). The selection of specific inhibitors of the SarA protein is made possible as a result of the identification of the binding sites of SarA protein on at least a portion of the agr (accessory gene regultor) gene, a gene that like the sar (staphylococcal accessory regulator) gene, plays a role in the virulence of Staphylococcus.

There is a great and urgent need among infectious-disease specialists, who have begun seeing one of their worst nightmares come true. They may be losing their last line of defense against the dangerous pathogen *Staphylococcus aureus* (*S. aureus*), which causes infections ranging from skin abscesses to such life-threatening conditions as pneumonia, endocarditis, septicemia, and toxic shock syndrome. Roughly one-third of the strains currently isolated from patients who acquire *S. aureus* infections while hospitalized are resistant to all antibiotics but one, vancomycin and now resistance to that antibiotic is cropping up. The present invention provides a new approach to combating *S. aureus* that may sidestep the organism's ability to develop resistance.

Despite intensive research efforts over the past 50 years, Staphylococcus, particularly *Staphylococcus aureus*, remains a serious threat to human health. In fact, recent reports describe clinical isolates with reduced susceptibility to vancomycin. Therefore, *S. aureus* represents a bigger threat to human health now, than at any time since the pre-antibiotic era.

Staphylococcus is an opportunisitic bacteria that takes advantage of immunocompromised subjects and may become pathogenic in these subjects. There are approximately thirty-two species of Staphylococcus with only three consistently causing human disease. *S. aureus* is clearly the most prominent disease causing species, followed by *S. epidermidis*, and in a distant third is *S. saprophyticus*. *S. epidermidis* is becoming more prominent as a disease causing species because it causes infections of in-dwelling medical devices. As a result, researchers are looking more carefully at *S. epidermidis*, and as a result of this research, have found homologs of both the sar and agr genes in *S. epidermidis*. Fluckiger, U., et al. (1998). Otto,M., et al. (1998), respectively.

*S. aureus* can cause a diverse array of diseases ranging from relatively superficial infections of the skin (boils) to infections of the eye (endopthalmitis) to life threatening osteomyelitis, endocarditis and toxic shock syndrome (reviewed by Projan and Novick, 1997). *S. aureus* is armed with a large battery of virulence factors that enable it to colonize a human host and cause a variety of disease states (reviewed by Projan and Novick, 1997). Nosocomial infections are of particular concern for two reasons. The first is that the majority of life-threatening infections arise in the hospital environment. For example, while the frequency of *S. aureus* infections incurred during orthopedic or cardiac implant surgery is steady, the overall number of infections has risen dramatically in the past decade. This is largely due to the increase in the frequency of these procedures. *S. aureus* has an amazing capacity to colonize in-dwelling prosthetic devices. The second reason for increased concern of *S. aureus* infections is that strains of methicillin-resistant *Staphylococcus aureus* (MRSA) are endemic in hospitals. Moreover, strains with some resistance to vancomycin emerged in the United States in 1997 (Tenover et al., 1998; Smith et al., 1999; Sieradzki et al., 1999). Therefore, the need for new, effective treatments for this drug resistant pathogen is urgent.

The variety of virulence factors expressed by *S. aureus* contribute to a highly efficient system for survival. Early in the infection, surface proteins are predominantly expressed. Protein A and the adhesins (e.g., collagen, fibronectin) are representative surface proteins that solve two problems for the *S. aureus* cell. First, they bind to extracellular matrix components and anchor the cell to the host tissue. Second, they provide a host protein camouflage which helps the infecting cell elude the host's immune system. The nascent colony increases in size until a critical number of cells is achieved (quorum) and a switch is thrown to re-organize the expression of virulence factors from surface proteins to exoproteins. These latter factors contribute to sequestration of the colony within a protective biofilm and enzymatic degradation of host tissue with an army of digestive enzymes, such as nucleases, lipases and proteases, which eventually result in an abscess. These enzymes accomplish two important functions or the bacterium: (1) allowing space for growth of the colony by getting rid of host tissue and (2) digested host tissue is assimilated by the bacterial cells for growth. Deep-seated abscesses, such as those found in staphylococcal ostemyelitis and endocarditis, often require surgical intervention to remediate the disease. It is important to note that this phenotypic switching process can be largely recapitulated in the laboratory environment, with surface protein expression occurring in the early log phase of a culture's growth and exoprotein expression occurring late in log and into the stationary phases of growth.

The potency of this pathogen can be attributed to the coordinated, temporally-regulated expression of a wide array of virulence factors. Early in infection expression of surface proteins predominates, e.g., the collagen and fibronectin adhesins and protein A. The surface proteins allow the organism to attach to host tissues and evade the immune system. However, when the concentration of *S. aureus* cells at the site of infection becomes high, surface protein expression is reduced and exoprotein expression increases. The temporal regulation of surface proteins and exoproteins can be recapitulated in laboratory culture growth models, where early log phase growth represents an early infection and stationary phase represents late infection. Using this model system and classical genetics, two major pleiotropically-acting regulatory loci that govern temporal expression of surface proteins and exoproteins have been identified: agr, for accessory gene regulator (Recsei et al., 1986; Morfeldt et al., 1988; Peng et al., 1988) and sar, for staphylococcal accessory gene regulator (Cheung et al., 1992; Cheung and Projan, 1994). Mutations in these loci result in aberrant regulation of most virulence factors (e.g., lipase, coagulase, α-toxin, adhesins, etc), which is reflected in diminished virulence in animal models of staphylococcal disease (Projan and Novick, 1997).

A scheme depicting the agr locus and its encoded proteins is shown in FIG. 1. Divergent promoters (P2 and P3), separated by approximately 180 bp, are responsible for transcription of the agrBDCA operon and RNAIII/hld operon (Morfeldt et al., 1996). The four Agr proteins combine to make a quorum-sensing system that is homologous to many two-component signal transduction systems found in prokaryotic organisms (Ji et al., 1997). AgrB is a cell membrane-bound transporter/processor of the AgrD peptide. AgrD is a 46 amino acid peptide that is cleaved to an octapeptide pheromone, exported by AgrB, and specifically recognized by (Ji et al., 1997) the AgrC membrane-bound receptor. The AgrD octapeptide pheromone allows an *S. aureus* cell to signal its presence to other cells in the growing colony. As the colony grows, the concentration of pheromone (Agr D) increases and reaches a particular level. AgrC, also an integral membrane protein, is activated by pheromone binding. AgrC is thought to be a kinase that acts on AgrA by initiating a signal transduction pathway that is believed to include AgrA. Whereas the exact mechanism of AgrA action is unknown, it is important for up-regulation of virulence gene expression and is thought to activate expression of the agr operon (RNAII) and the divergently expressed RNAIII. It is clear, however, from the work of Arvidson's group (Morfeldt et al., 1996) that AgrA does not bind DNA either in the presence or absence of SarA. Mutations in any of the agr open reading frames (ORFs A, B, C, D) eliminate the up-regulation of RNAII and RNAIII expression (Novick et al., 1995). Additionally, agrA mutants have dramatically reduced virulence in animal models of staphylococcal arthritis, osteomyelitis, endocarditis and endopthalmitis (Abdelnour et al., 1993; Cheung et al., 1994a; Gillaspy et al., 1995; Booth et al., 1995). RNAIII is a regulatory RNA species, the function of which is not completely clear. However, there is evidence that RNAIII directly regulates expression of some *S. aureus* virulence genes by an anti-attenuation mechanism (Novick et al., 1993; Saravia-Otten et al., 1997).

In summary, when *S. aureus* attaches to a host tissue, a small amount of the AgrD pheromone is released. Early on, the concentration of the pheromone is too low to affect AgrC kinase activity. However, once the number of cells has risen, the local concentration of pheromone increases to a level whereby AgrC becomes activated. At this point the phenotypic switch is thrown and exoprotein expression dramatically increases.

Mutations in agr leads to decreased expression of exoprotein virulence factors and significantly reduced virulence in animal models of staphylococcal arthritis, endocarditis, osteomyelitis and endopthalmitis (Abdelnour et al., 1993; Cheung et al., 1994a; Gillaspy et al., 1995; Booth et al., 1995, respectively). Inhibition of the agr quorum-sensing/virulence gene activating system is a goal of the present invention. Since agr is activated by a transcriptional regulator, SarA, the present invention is directed to inhibiting this protein.

The second regulatory locus, sar, encodes a 14.4 kDa protein: SarA, also depicted in FIG. 1. Mutations in sar, like those in agr, lead to dramatically decreased virulence in animal models of staphylococcal disease (Cheung et al., 1994a). Interestingly, agr⁻, sar⁻ double mutants are less virulent than either of the single mutants in staphylococcal endocarditis, endophthalmitis and osteomyelitis (Cheung et al., 1994b; Booth et al., 1997; Gillaspy, et al., unpublished). Presumably, this phenotype is because SarA regulates expression of both transcripts in the agr locus (agr and RNAIII; Cheung et al., 1997) and SarA also regulates virulence factor genes that fall outside of agr control. For example, the cna gene, encoding the collagen adhesin, is not affected by mutations in the agr locus, but is under sar control (Gillaspy et al., 1998; Blevins et al., 1999). agr mutants do not have altered sar mRNA accumulation, whereas agr mRNA expression is dramatically affected by sar mutations (Cheung et al., 1997; Gillaspy and Smeltzer, unpublished). Specifically, there is a significant diminution of agr mRNA and nearly a complete loss of RNAIII in the sar strain ALC136 when compared to the wild type strain RN6390 (Cheung et al., 1997). The same observation has been made in clinical isolates in which the sar gene has been mutated (Gillaspy and Smeltzer, unpublished).

SarA present in crude extracts of *S. aureus* (Morfeldt et al., 1996) or recombinant SarA in *E. coli* extracts (Heinrichs et al., 1996) or purified, recombinant SarA (Chein and Cheung, 1998; U.S. Pat. No. 5,587,288; Rechtin et al, 1999,) have been shown to bind the DNA region of the agr promoters (this region also is referred to herein as the agr enhancer). AgrA has not been shown to bind DNA and was not present in the SarA-agr enhancer complexes (Morfeldt et al.,1996).

Arvidson and his colleagues recently reported that SarA is a DNA-binding regulatory protein and that its binding sites were located cis to the P2 and P3 promoters in the agr locus, a region that is referred to as the agr enhancer (Morfeldt et al., 1996). The agr enhancer has inverted repeats of a 7 bp sequence 5'-CTTAAGT-3' (FIG. 2). Qualitative electrophoretic mobility shift assays (EMSA) were used to examine this region for regulatory proteins that may bind. Crude extracts of *S. aureus* wild type, sar⁻ and agr⁻ mutants were prepared. DNA fragments containing the left half of the region, right half of the region and the entire region were used in the EMSA tests. The migration of all of these fragments was retarded in native gels containing wild type and agr⁻ extracts, but not sar⁻ extracts. Furthermore, DNA affinity chromatography was used to purify the regulatory protein species and one protein with a MW of approximately 15 kDa was recovered. The amino acid sequence of the first 20 residues of that protein was determined and it matched that of the protein encoded by the sar gene. A simple model for SarA-mediated activation of genes in the agr locus would have SarA protein binding to a site that includes the heptad repeats and facilitating the binding of RNA polymerase to the adjacent promoters. However, complicating any simplified model is recent data from Rechtin et al. (1999) that unambiguously shows using high-affinity DNase I footprint analysis that the heptads are not the primary binding sites for SarA. Rather SarA protected three distinct, bipartite sites from DNase I digestion at extremely low protein concentrations, indicting very high affinity binding.

Production of the three distinct transcripts arising from the sar operon are regulated temporally (Bayer et al., 1996; Blevins et al., 1999). However, all three transcripts include the SarA ORF. Like agrA mutations, transposon insertions in the SarA ORF also eliminate induction of RNAII and RNAIII in late phase growth and result in reduced staphylococcal virulence in animal models of disease (Cheung et al., 1994 a and b; Booth et al., 1997). In seminal biochemical work in this area, SarA was shown to be a DNA-binding protein that is capable of binding DNA fragments containing cis regulatory elements for the promoters of both the agr operon (RNAII, P2 promoter) and the RNAIII operon (P3 promoter) (Morfeldt et al., 1996). Heptad repeats were identified upstream of both P2 and P3 promoters and were proposed to be SarA binding sites (see FIG. 2 and FIG. 3). A DNA fragment containing the RNAIII gene and 93 bp upstream of the transcription start site, including the heptad repeats, was sufficient for regulated expression of RNAII (see pEX085 in FIG. 3). Furthermore, removal of the distal half of the sequences upstream of the P3 promoter, including one heptad, eliminated appropriate expression of RNAIII (see pEX082 in FIG. 3). In addition, a synthetic DNA fragment including the repeats was bound by SarA in electrophoretic mobility shift assays (EMSA) in vitro using *S. aureus* extracts and was used successfully to purify SarA from extracts by DNA-affinity chromatography (Morfeldt et al., 1996).

In a more recent report, SarA, expressed as a GST-fusion protein in *E. coli* and purified, was observed to have relatively low affinity for DNA fragments containing the heptad repeats (Chien and Cheung, 1998). Furthermore, DNase I footprinting revealed a primary binding site for SarA in the inter-promoter region (see FIG. 3) that did not include the heptad repeats in the fragment cis to the P3 promoter shown to be sufficient for appropriate expression of RNAIII by Morfeldt et al. (1996). These two published reports of SarA interactions with the agr region have inconsistent conclusions regarding the binding sites for SarA in the agr locus (Morfeldt et al., 1996; Chien and Cheung, 1998). In the earlier report, approximately 60 bp upstream of the P3 promoter was shown to be sufficient for appropriate, regulated expression of RNAIII expression in *S. aureus* (Morfeldt et al., 1996). In addition, Morfeldt et al. (1996) proposed that SarA likely interacts with the regulatory regions containing the 7 bp repeats immediately upstream of the P3 and P2 promoters (see FIG. 2). However, in the latter report a DNase I footprint in the inter-promoter region using a recombinant fusion of GST-SarA was observed that had no overlap with the regulatory region described in the early report (Chien and Cheung, 1998).

The results of Chien and Cheung (1998) reporting an in vitro study of SarA-agr interactions may not be indicative of true SarA-agr interactions because of the nature of the protein used for the study. A GST-SarA fusion was used for most of the work and it appears that this construct most likely yielded an inactive SarA protein for two reasons: 1) After calculations of the concentrations of protein used in the EMSA and DNase I experiments reported in Chien and Cheung (1998), it became clear that micromolar amounts of SarA were required to achieve mobility shifts or footprints, respectively. This is a very high concentration of a DNA-binding protein. In the present invention, picomolar concentrations resulted in similar shifts in EMSA or footprints in DNase I protection experiments. Thus, the SarA protein used in the present invention appears to be several orders of magnitude more active than the protein used by Chien and Cheung. 2) Most importantly, to examine the monomer-dimer equilibrium for SarA, fluorescence anisotropy was used (Fernando and Royer, 1992; Maleki et al., 1997). For this work a fluorescent dye is coupled to the protein, typically the amino terminus. Fluoroscein, fluorescein with a six-carbon spacer and dansyl, independently, were coupled to the amino terminus of SarA, and in each case, a rapid inactivation of SarA was found as a result of unfolding (Hurlburt, unpublished). These dyes have been used in anisotropy experiments with several proteins previously without any problems (Maleki et al., 1997; Hurlburt unpublished). Thus, it was concluded that the amino terminus of SarA is intimately involved in SarA's structural integrity and resultant activity. The determined low-resolution structure of SarA in the present invention shows that the amino terminus is proximal to the most likely DNA-binding domain of the protein. The SarA-GST fusion used by the Cheung group was to the amino terminus and it is strongly suspected that the low activity of the protein used in those studies was a result of the fusion.

In recent work, the quorum sensing mechanism encoded by the agr operon was inhibited and mice became protected from infection by *S. aureus* (Balaban et. al., 1998). This group approached the problem by targeting the quorum sensing signal molecule and its receptor. They looked at inhibitors of agr activation; i.e., the octapeptide pheromone and/or the 36 kDa protein. However, Richard Novick's group reported that this kind of approach has a serious limitation (Ji et al., 1997). Namely, strains of *S. aureus* can be grouped based on whether they activate or inhibit the quorum sensing system encoded by agr. In other words, all strains autologously activate their own agr expression, but RN6390 inhibited agr expression in strains SA502, RN7843, RN8462 and RN8463, and vice versa in a process they termed bacterial interference. This likely is due to co-evolution of the signal molecule and its receptor. Apparently, the signal molecule from one strain inhibits the receptor of another, non-compatible strain. Thus, the Balaban approach may have limited efficacy against some strains of *S. aureus*.

The present invention approaches the treatment of staphylococcal virulence and infection differently than previous publications by the inhibiting the activation of agr gene expression by inhibiting SarA function resulting in the inhibition of the expression of staphylococcal virulence factors. The present method of treatment provides a way to attenuate staphylococcal virulence which is believed to be more widely applicable than the Balaban inhibitor. This is so because SarA and its target DNA sequences cis to agr do not suffer as much strain variability as the Balaban inhibitor. Moreover, since the agr locus also includes RNAIII, a known regulator of virulence gene translation, inhibiting agr gene expression will have a more profound effect than inhibition of the quorum sensing system alone as disclosed by Balaban.

The present invention provides a novel method of treating staphylococcal diseases by interfering with the production of virulence factors, which in turn, prevents the Staphylococcus species from becoming a potent pathogen. The present invention is directed to designing, synthesizing and identifying potent inhibitors of SarA function and using these inhibitors to treat staphylococcal infections.

SUMMARY OF THE INVENTION

The present invention is directed to inhibitors of staphylococcal SarA protein function involved in the expression of staphylococcal virulence factors and the use of these inhibitors to treat and prevent staphylococcal infections in subjects. Particularly, the inhibitors act to interfere with the binding of the SarA protein to its binding site(s). The selection of specific inhibitors of the SarA protein is made possible as a result of the identification of the binding sites of SarA protein on at least a portion of the agr (accessory gene regulator) gene, a gene that like the sar (staphylococcal accessory regulator) gene, plays a role in the virulence of staphylococci species.

The present invention further is directed to a method of identifying inhibitors of SarA function involved in the expression of staphylococcal virulence genes comprising a) contacting a candidate inhibitor with at least one SarA binding site of the agr locus in solution to allow the binding reaction to equilibrate for a sufficient period of time; and b) assessing the binding of said candidate inhibitor to the SarA binding site of the agr locus.

The present invention further is directed to a method of identifying inhibitors of SarA function involved in the expression of staphylococcal virulence genes comprising a) contacting a candidate inhibitor with SarA in solution to allow the candidate inhibitor to affect the ability of SarA to bind to at least one SarA binding site of the agr locus; b) contacting said solution of step a) with at least one SarA binding site of the agr locus either simultaneously with the contact of said inhibitor and the SarA or subsequently to the contacting of the inhibitor and the SarA; and c) assessing the inhibition of the candidate inhibitor on the SarA binding to the SarA binding site of the agr locus.

DETAILED DESCRIPTION OF THE PREFERRED EMBODIMENT

Figure 1:
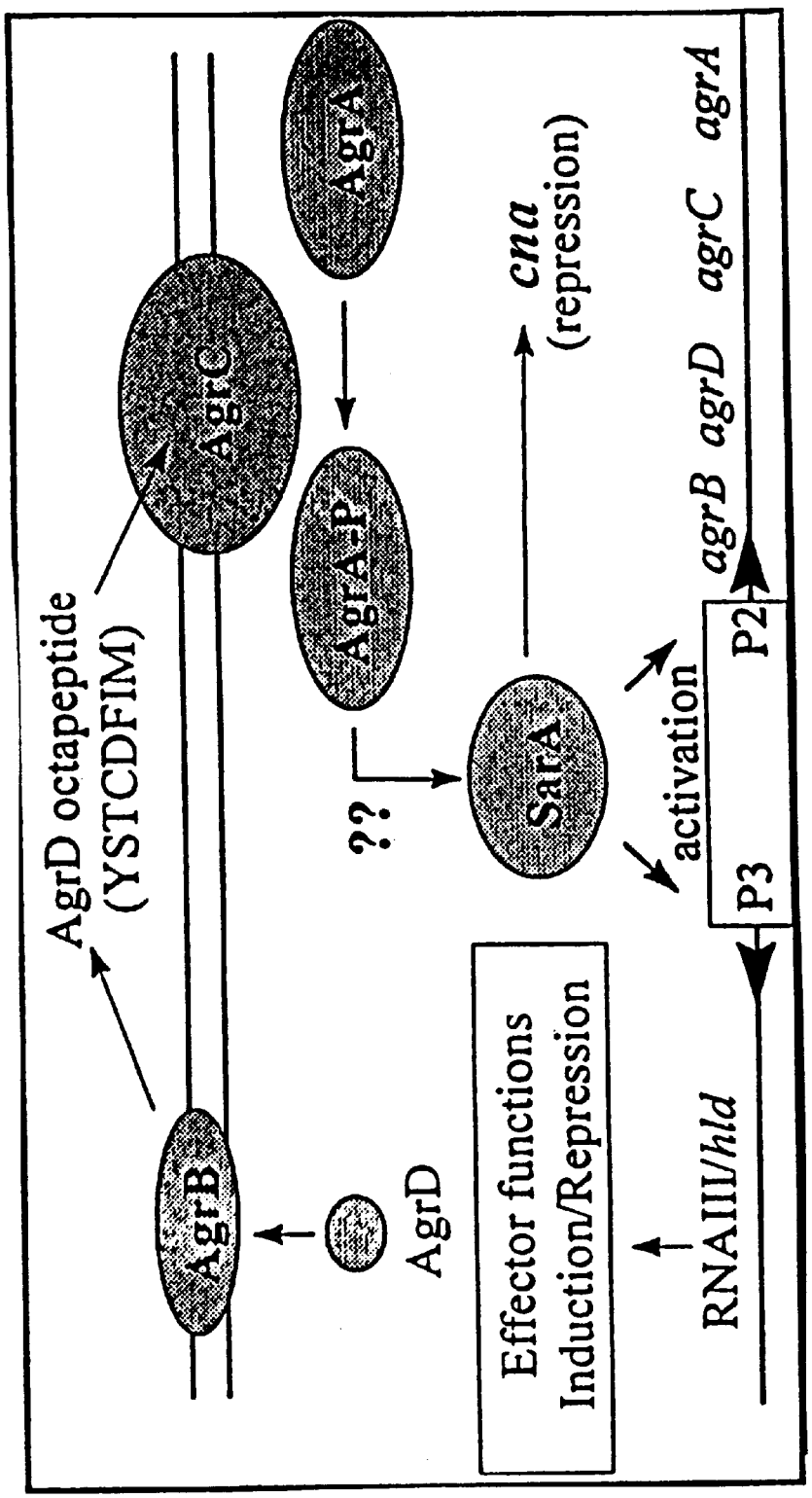
FIG. 1 depicts a scheme of SarA and Agr roles in virulence gene expression. Four Agr proteins comprise a quorum sensing system. RNAIII regulates virulence gene expression at the translational level and SarA is responsible for activation of agr and RNAIII expression (SEQ ID NO:20).

The present invention combines genetic, biochemical and structural studies to define the mechanism by which SarA controls expression of the genes in the agr locus. The agr locus includes agrDCBA, RNAIII/hld (See FIG. 1). This work, in turn, allows the design and synthesis of inhibitors of SarA arnd the testing of the effects of these inhibitors of SarA and its regulated virulence genes with a major emphasis on the development of novel anti-staphylococcal therapeutics to combat the onslaught of drug resistant staphylococcal pathogens.

The present invention is directed to inhibitors of SarA function involved in the expression of staphylococcal virulence genes and a method of treating a staphylococcal infection comprising administering to a subject having a staphylococcal infection at least one inhibitor of SarA function involved in the expression of staphylococcal virulence genes. The inhibitor is designed to interfere with SarA mediated activation of the agr locus and more specifically the inhibitor interferes with the binding of SarA to at least a portion of the agr locus. The portion of the agr locus is composed of greater than about 70% adenosine-thymidine (A-T) nucleotides, more preferably at least about 75% A-T nucleotides, and most preferably between about 79% and 89% A-T nucleotides. More specifically, the inhibitor interferes with the binding of SarA to at least a portion of the agr locus depicted in FIG. 3. The inhibitor is designed to interfere with the binding of SarA to at least one of the portions of the agr locus depicted in FIG. 3 that contains a nucleotide sequence selected from the group consisting of at least the nucleotide sequences in the A1 and A2 boxes, at least the nucleotide sequences in the B1 and B2 boxes and at least the nucleotide sequences in the C1 and C2 boxes. Further, the inhibitor also interferes with the binding of SarA to the intervening nucleotide sequences between the A1 and A2 boxes when the inhibitor binds to the nucleotide sequence in the A1 and A2 boxes, to the intervening nucleotide sequences between the B1 and B2 boxes when the inhibitor binds to the nucleotide sequences in the B1 and B2 boxes or to the intervening nucleotide sequences between the C1 and C2 boxes when the inhibitor binds to the nucleotide sequences in the C1 and C2 boxes. The most preferred inhibitors of SarA binding bind to at least a portion of the agr locus, and the most preferred inhibitors are oligonucleotide analogs that utilize the Watson & Crick basepairing to bind to nucleic acids, such as peptide nucleic acid molecules, DNA molecules, RNA molecules, phosphothiolate oligonucleotides, and anti-sense oligonucleotides. Hairpin polyamides are also preferred inhibitors of the present invention. Any molecules that can enter a staphylococcus and interfere with the SarA function in the expression of staphylococcal virulence factors are encompassed by the present invention. Such molecules can be synthesized, tested and identified utilizing the methods disclosed in the present invention. The inhibitor is admixed with an acceptable carrier, such as a pharmaceutically acceptable carrier for administration to the subject having a staphylococcal infection. The pharmaceutically acceptable carrier may contain preservatives and other non-immunogenic additives, according to methods well known in the art. See, e.g. Remington's Pharmaceutical Sciences: Drug Receptors and Receptor Theory, (1990). The carrier may contain additives that are known to facilitate the movement of the inhibitor into the staphylococci without adversely affecting the subject treated. Such additives are known to skilled persons or can be selected using known methods. These additives facilitate the movement into the cell of inhibitors that do not readily cross cell membranes, and peptides are known additives that facilitate such movement across the cell membranes.

The inhibitors of the present invention are intended for use in treating all staphylococcal infections. As discussed above, *S. aureus, S. epidermidis* and *S. saprophyticus* are the three disease causing species. It is known that *S. aureus* and *S. epidermidis* have homologs of both the sar and agr genes. The sequences of these genes in other species of staphylococci are used to prepare inhibitors of SarA function in these species. Likewise SarA itself is used to develop inhibitors that inactivates SarA so that it cannot bind to the agr locus.

The following comparison shows that the SarA protein from *S. aureus* and *S. epidermidis* are quite similar.

```
SEQ ID NO:1   Sara S. aureus   MAITKINDCFELLSMVTYADKLKSLIKKEF
                               |||:|||||||||:||||||:||::|||||
SEQ ID NO:2   Sara S. epi      MAISKINDCFELLAMVTYADRLKGIIKKEF SISFEEFAVLTYISENKEKEYYLKDIINHLNYKQPQVVKAVKILSQEDYFDKKRNEHDER
              ||||||||||||||||||:||||||||||||||||||||||| ||||:||:|||||||||
              SISFEEFAVLTYISENKEEEYYLKDIINHLNYKQPQVVKAVKNLSQENYFNKKRNEHDER TVLILVNAQQRKKIESLLSRVNKRITEANNEIEL
              ||||||:::|||||::||:|||:||||||||| |:
              TVLILVDSKQRKKIDDLLKRVNNRITEANNENEV
```

The present invention also is directed to a method of identifying inhibitors of SarA function involved in the expression of staphylococcal virulence genes comprising: a) contacting a candidate inhibitor with at least one SarA binding site of the agr locus in solution to allow the binding reaction to equilibrate for a sufficient period of time; and b) assessing the binding of said candidate inhibitor to said SarA binding site of the agr locus. (See FIG. 15 for an example of the results of this method.) The method further comprises the addition of SarA to the solution of step a) simultaneously with the inhibitor and the SarA binding site, and then an assessment of the binding affinity of the candidate inhibitor relative to the binding affinity of the SarA to the SarA binding site of the agr locus. Alternatively, the addition of SarA to the solution of step a) is sequentially with the inhibitor and the SarA binding site, and then the assessment of the binding affinity of said candidate inhibitor relative to the binding affinity of said SarA to the SarA binding site of the agr locus. (See FIG. 16 for an example of the results of this method showing the results with and without the addition of SarA.)

The assessment of binding or the lack of binding of the inhibitor to the SarA binding site and/or of SarA to the SarA binding site is performed by an electrophoretic mobility shift assay (EMSA) described herein and in Rechtin et al. (1999). An additional method for assessing the binding of the inhibitor and SarA to the SarA binding site is fluorescence anisotropy (Nikiforov et al., 1999).

An inhibitor within the meaning of the present invention should have a $K_D$ of less than about 1 nM. However, a lower $K_D$ in the pM range is more preferred. The $K_D$ should be low enough for an inhibitor of SarA binding sites to bind to the extent that SarA cannot bind to these sites. In an EMSA, as the inhibitor concentration increases, the SarA-SarA binding site complex decreases. If the inhibitor is PNA then the DNA (i.e., SarA binding site)-PNA complex increases. If the inhibitor acts on SarA alone and does not bind to the SarA binding site, then the free or unbound DNA (SarA binding site) increases. (See the results in FIG. 16).

Figure 3:
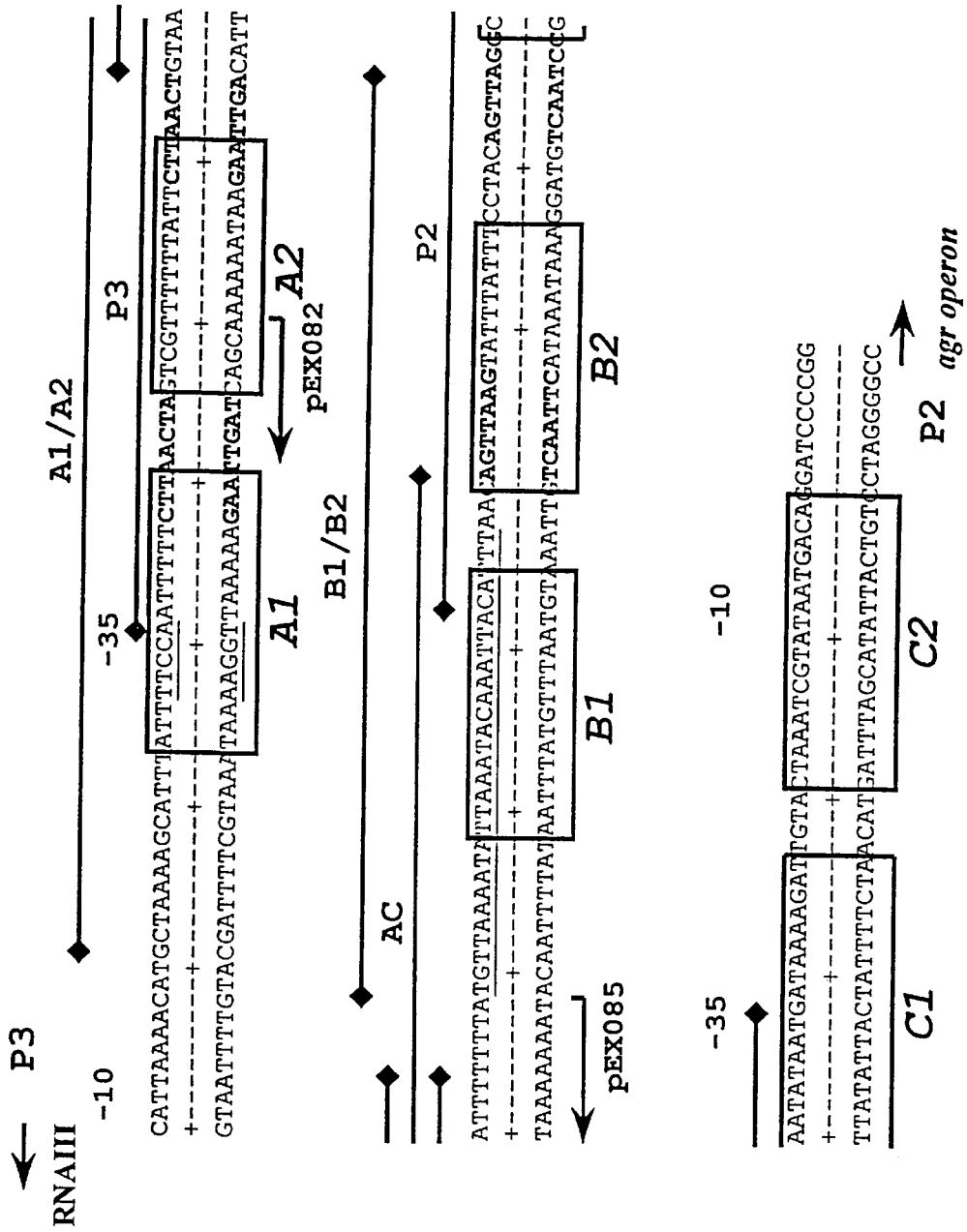
FIG. 3 depicts the sequence of the P2–P3 promoter region, footprints from DNase I studies and DNA fragments used in the present invention (SEQ ID NOS:10 and 11). The diagram shows the DNA sequence of the P2 and P3 promoters and the intervening region. The protected areas from the DNAse I footprinting experiments are indicated by the boxes and are labeled A1, A2, B1, B2, C1 and C2. The regions corresponding to nucleotide sequences used for quantitative EMSA are indicated by the lines above the sequence and are labeled A1/A2, B1/B2, P2, P3 and AC. The heptad repeats reported by Morfeldt et al. (1996) are shown in boldface type. The DNase I footprint reported by Chien and Cheung (1998) is underlined. The upstream ends of the RNAIII/P3 promoter constructs, pEX082 and pEX085, used by Morfeldt et al. (1996) for complementation studies are indicated below the sequence.

Specifically the SarA binding site of the agr locus that is useful in the present method is at least one nucleotide sequence selected from the group consisting of at least the nucleotide sequences in the A1 and A2 boxes, at least the nucleotide sequences in the B1 and B2 boxes and at least the nucleotide sequences in the C1 and C2 boxes as depicted in FIG. 3.

Additionally, the present invention includes a method of identifying inhibitors of SarA function involved in the expression of staphylococcal virulence genes comprising a)

contacting a candidate inhibitor with SarA in solution to allow the candidate inhibitor to affect the ability of SarA to bind to at least one SarA binding site of the agr locus; b) contacting the solution of step a) with at least one SarA binding site of the agr locus either simultaneously with the contact of the inhibitor and the SarA or subsequently to the contact of theinhibitor and the SarA; and c) assessing the inhibition of the candidate inhibitor on the SarA binding to the SarA binding site of the agr locus. This method allows the assessment of the inhibitor directly on the SarA rather than the effect of the inhibitor on the SarA binding site. This method uses the assessment of binding of the inhibitor to the SarA binding site by an electrophoretic mobility shift assay. The SarA binding site of the agr locus used in this method is preferably a nucleotide sequence selected from the group consisting of at least the nucleotide sequences in the A1 and A2 boxes, at least the nucleotide sequences in the B1 and B2 boxes, at least the nucleotide sequences in the C1 and C2 boxes and a combination therof as depicted in FIG. 3.

The present invention targets the expression of genes in the agr locus directly, by inhibiting SarA-mediated activation. This approach offers advantages over known approaches because SarA is a pleiotropically-acting regulator that controls another pleiotropically-acting regulator. By inhibiting SarA, agr will be inhibited as well as any other genes under SarA control (e.g., collagen adhesin, cna, Gillaspy et al., 1998). Synthetic molecules that inhibit protein-DNA interactions have been developed and show tremendous promise for pharmaceutical applications. These molecules include peptide nucleic acid (PNA, Corey, 1996) and hairpin polyamides (HP, White et al., 1998). Both PNA and the HP bind dsDNA with very high specificity and affinity. These molecules have great potential for anti-staphylococcal therapies once appropriate targets are identified. Molecules like PNAs and HPs that are designed to bind in the agr regulatory region and inhibit SarA-mediated activation of genes in the agr locus are considered to be inhibitors of SarA function within the meaning of the present invention. Because of the high affinity (sub-nanomolar $K_D$), very low amounts of the drug or SarA function inhibitor needs be used in a subject in need of treatment. Furthermore, if the subject is to receive a prosthetic device (e.g., heart valve or hip), the drug could be used prophylactically to inhibit S. aureus colonization. The inhibitor can be administered prior to surgery or can be impregnated in beads for slow release and packed around a prosthetic hip device for a while for local administration. Techniques are known for impregnating beads or substrates with drugs. These beads or substrates may be biodegradable.

The present invention is premised upon the determination of the interactions of SarA with the P2–P3 regulatory region, the determination of the mechanism by which SarA regulates virulence gene expression in Staphylococcus, and the biochemical characterization of SarA and its interaction with DNA. In the present invention, a full-length SarA in E. coli was expressed without heterologous fusions and purified to homogeneity. It was determined that SarA was a dimer in the presence or absence of DNA and was comprised primarily of α-helices. The combined results of DNaseI footprinting and quantitative EMSA experiments indicate that three SarA binding sites exist. Two of the footprints overlap elements of the P2 and P3 promoters. All of the protected sequences included portions of the heptad repeats described by Morfeldt et al. (1996). One SarA dimer was found to bind each binding site with very high affinity. Three dimers bind the entire region and produce an unusual laddering pattern in electrophoretic mobility shift assays (EMSAs).

Based in part upon the results disclosed in the present application and the crystal structure of SarA, it is believed, but applicants do not wish to be bound by this theory, that SarA utilizes "indirect readout" in it recognition of DNA biding sites. This mechanism of binding site recognition relies on the 3-dimensional structure of the DNA (agr locus) of the SarA binding site(s) to place the phosphate backbone in a particular configuration. It is this configuration that is bound with high affinity by the protein. This binding mechanism is similar to the binding site recognition of the trp repressor of E. coli. This type of binding mechanism is the opposite of "direct readout" in which the functional moieties in the major groove DNA are bound by components of the binding protein.

The following provides the experiments and results that define the specific SarA binding sites on the agr locus and their use in producing and selecting appropriate inhibitors of SarA function, and more particularly, appropriate inhibitors of SarA binding to the agr locus. These molecules, preferably PNA and HP, are designed to interrupt SarA-agr interactions.

EXAMPLES

The examples presented below include the following experiments required as a prerequisite to designing and preparing inhbitors that disrupt SarA and agr function: i) cloned the sar genes from the main laboratory strain of S. aureus, as well as 30 clinical isolates, ii) expressed the sar gene in E. coli and purified the SarA proteins from strains DB and RN6390, iii) established a quantitative assay for SarA-DNA interactions (electrophoretic mobility shift or EMSA), iv) mapped the binding sites for SarA within an important agr regulatory region using DNase I footprinting, v) determined the equilibrium binding constants ($K_D$) for SarA and putative target sites in the agr enhancer region, vi) determined that SarA is a dimer using chemical cross-linking and dynamic light scattering, vii) grew high quality crystals of SarA, in the presence and absence of DNA, for structure determination, viii) solved structures of the protein alone and of the protein-DNA complex to 2.5 and 2.9 angstrom resolution, respectively, and ix) generated preliminary images of SarA bound to the agr regulatory region by atomic force microscopy. For most of these studies both the DB and RN6390 SarA proteins were used and gave equivalent results. The majority of these results are described in (Rechtin et al., 1999), which is herein incorporated in its entirety by reference.

Cloning, Expression and Purification of SarA

As reported by Bayer et al. 1996, there are at least two naturally occurring variants of the SarA protein inferred from the gene sequence. Strain RN6390 encodes a SarA protein that is eleven amino acids shorter than the SarA from strain DB. There is also a phenylalanine to leucine substitution at position 53 in the DB protein. S. aureus chromosomal DNA was isolated as described by Smeltzer et al. (1996).

Synthetic DNA primers were used for PCR amplification that incorporated restriction enzyme sites for subsequent cloning in plasmid vector pET9a. The SarA coding region was amplified using PCR from S. aureus strain DB with primers incorporating NdeI and BamHI restriction enzyme sites:

SEQ ID NO:3 NdeI 5'GGGAGGTTTTACATATGGCAATTA-CAAAAATC3'

SEQ ID NO:4 BamHI-5'GTTTAATAGAATGGATCCTCTAT-CAAACTTCACC3'.

The PCR products from reactions using RN6390 and DB chromosomal DNA were appropriately restricted with NdeI and BamHI and ligated into likewise restricted pET9A (Novagen) to yield pET-RN and pET-DB plasmids. The fidelity of the constructs was confirmed by DNA sequencing. When the optical density of the culture was 0.4 at 600 nm at 37° C., IPTG induction (final concentration of 1 mM) of E. coli LB broth cultures,(E. coli strain BL21(DE3)pLys) carrying these expression constructs was performed. Maximal expressio occurred within 3 hours of induction.

Cells were collected by centrifugation, 5,000×g, 10 min., 4° C. and cell pellets were frozen at −20° C. Cells were lysed in 50 mM Tris-HCl, pH 7.5, 1 mM DTT, 1 mM EDTA, 1 mM PMSF on ice. Chromosomal DNA was sheared with ultrasound treatment and the insoluble debris was removed by centrifugation, 15,000×g, 30 min., 4° C. The cleared lysate was brought to 70% saturation with solid ammonium sulfate and the insoluble material removed by centrifugation 15,000×g, 30 min., 4° C. The soluble supernatant was twice subjected to dialysis against at least 100 volumes of HSB-150 (HSB=20 mM Tris-HCl (pH=7.6), 1 mM EDTA, 1 mM DTT, and 150 mM NaCl). The resultant solution was loaded on a heparin-Sepharose column (50 mL bed volume) and washed with at least 300 ml of HSB-150. Proteins were eluted with a linear gradient of HSB-150 to HSB-1500 (HSB with 1.5 M NaCl). Total volume of the gradient was 400 mL. Column fractions were analyzed for the presence of SarA using Tricine SDS-PAGE and peak fractions were pooled.

Figure 4:
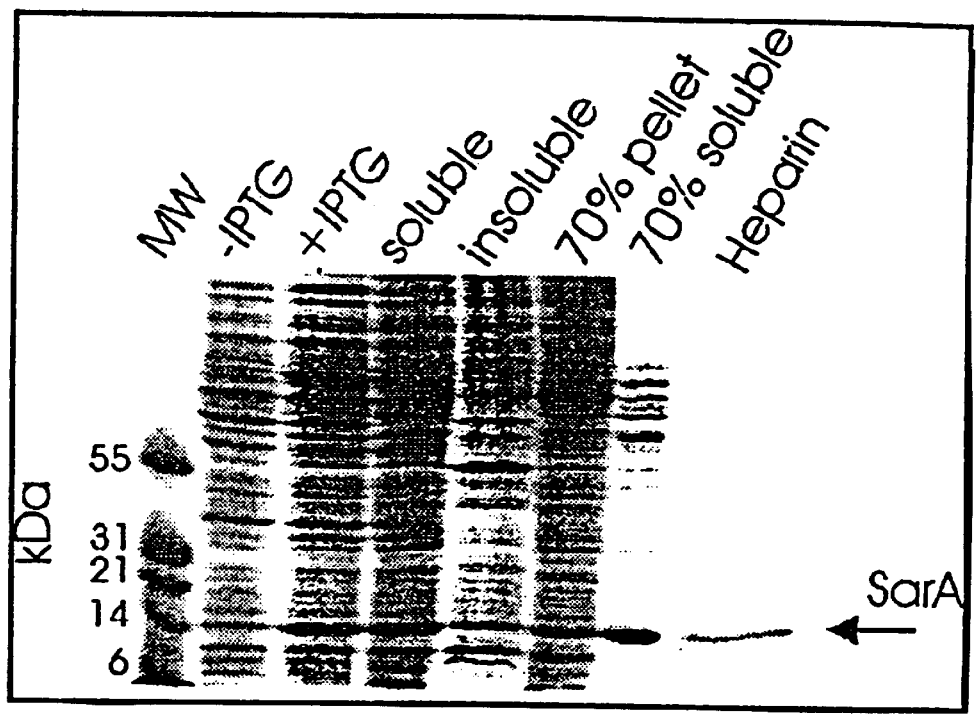
FIG. 4 depicts the purification of SarA from *E. coli* Coomassie Blue stained gel. Pre vs. post induction, soluble supernatant vs. insoluble, soluble vs. insoluble in 70% ammonium sulfacte, pooled fractions after heparin-Sepharose chromatography.

A unique protein of approximately 15 kDa (recombinant SarA) was observed by SDS-PAGE analysis (FIG. 4). Following examination of several standard purification approaches, a simple one-day preparation that yields SarA that is at least 95% pure was selected (FIG. 4). The purification protocol involves a short induction time, lysis with ultrasound, precipitation of most contaminating proteins with ammonium sulfate, and ion exchange chromatography. It should be noted that the SarA used is an intact, full-length protein, not harboring fusions that may serve to alter the protein's activity. $NH_2$-terminal protein sequencing confirmed that the purified protein is SarA. The concentration of SarA monomer was determined spectrophotometrically at 280 nm using an extinction coefficient of 7740 $M^{-1}$, calculated using the method of Gill and von Hippel (1989) and absorbance at 280 nm. The DB and RN6390 SarA proteins express equally well and show no dramatic differences in the purification procedures. However, since the protein from the DB strain is more representative of clinically-relevant forms of SarA (discussed below), the remainder of the experiments shown below were done with DB SarA, unless indicated otherwise.

Purified SarA was stored at −20° C. and is stable for at least 6 months without noticeable loss of activity. Typical yield of SarA was 1–3 mg/liter of culture.

To determine the activity of the purified SarA stoichiometric binding conditions in EMSA with DNA fragment P3 (FIG. 3) was used. At DNA concentrations that are very high relative to the equilibrium dissociation constant ($K_D$), the amount of protein required to bind 50% of the available DNA is used to determine the concentration of active protein using the equation $K_D=[P]_{1/2}-\frac{1}{2}[DNA]_o$, where $[P]_{1/2}$ is the protein concentration at 50% saturation and $[DNA]_o$ is the total DNA concentration (Riggs et al., 1970; Hurlburt and Yanofsky, 1990). Under these conditions ([DNA]>10 nM), $K_D$ is insignificant and the equation simplifies to $[P]_{1/2}=\frac{1}{2}[DNA]_o$. Assuming that SarA binds to the P3 DNA fragment as a dimer (confirmed below), the activity of SarA in preparations prepared by the disclosed method is routinely 90–95% active of the value determined spectrophotometrically. The concentration of SarA reflects the concentration of active protein.

Oligomeric State of SarA

It was determined that SarA was a dimer using both chemical cross-linking and dynamic light scattering (DLS) and also with x-ray crystallography as shown below.

Chemical Cross-linking of SarA

Figure 5:
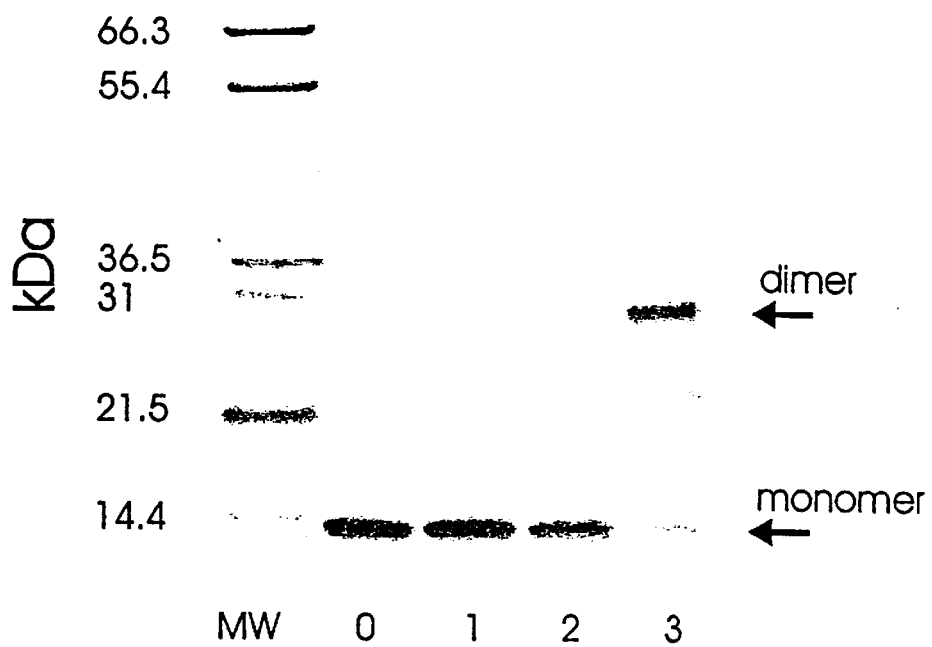
FIG. 5 depicts the chemical crosslinking of SarA.
Figure 5:
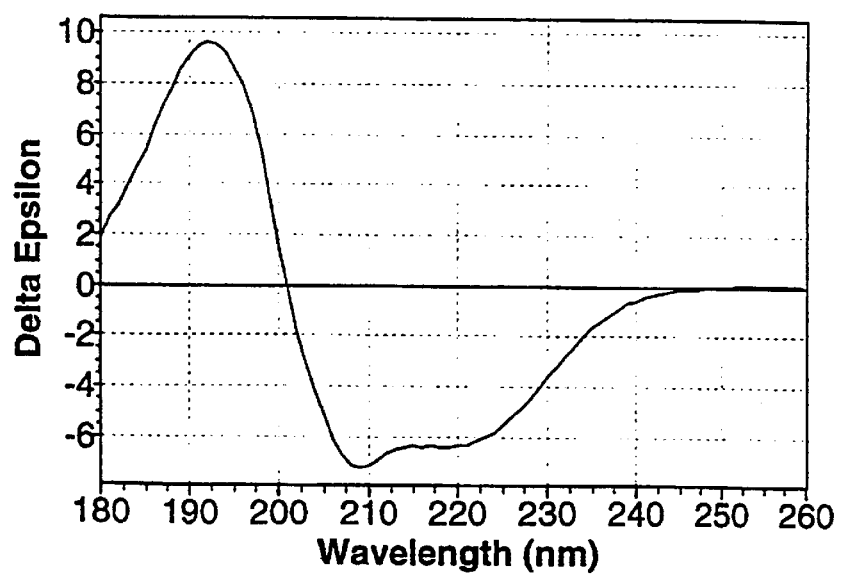

For chemical cross-linking, a 10 μM solution of SarA monomer was subjected to brief treatment with any the of the protein crosslinking agents, bis-(sulfosuccinimidyl) suberate ($BS^3$), disuccinimidyl suberate (DSS) and/or dithiobis (disuccinimidyl) (DSP) for various times in the absence or presence of agr DNA according to Maleki et al. (1997). In the case of DSP, DTT was excluded from the buffer. The reaction mixture contained 10 μM SarA and crosslinker in a total reaction volume of 30 μl. Reactions were allowed to proceed for 1 minute at 4° C. and quenched by the addition of 10 μl of 1 M Tris-Cl (pH=8.0). Denaturing loading dye was added to each reaction and incubated at 95° C. for 20 minutes. Reaction products were analyzed on a 12% Tricine-SDS-polyacrylamide gel and visualized by Coomassie blue staining. A product consistent with a SarA dimer was observed in FIG. 5A. A dimer is the only oligomer detected under any conditions tested. The presence of agr DNA had no effect on the cross-linking results. The DB and RN6390 SarA proteins behaved identically in this assay.

Dynamic Light Scattering

The oligomerization state of purified SarA was examined in the presence and absence of 10 mM $MgCl_2$ by dynamic light scattering (DLS) using a 2001 DynaPro Dynamic Light Scattering Instrument and analysis software, DYNAMICS, version 3.30. DLS reveals the homogeneity and oligomeric state of proteins in solution based on diffraction of visible light. Two sets of measurements were made with protein in the absence of $MgCl_2$. In the first, SarA was concentrated to 3.3 mg/mL (230 μM), which is necessary to provide the experimental signal, and in the latter to 11.7 mg/mL (813 μM), which is the concentration used in thecrystallization experiments (described below). It is important to note that the chemical cross-linking experiments were performed at much lower concentrations of SarA, concentrations at which DNA is completely bound in EMSA experiments. In each experiment, SarA (3.3 mg/ml) was buffered by solutions containing 50 mM Tris-HCl, pH 7.5; 2mM DTT; 500 mM NaCl; 1 mM EDTA. Twenty measurements were taken at 22° C. for each analysis. The bimodal analysis of the scattering revealed a monodisperse solution with a macromolecular weight of 34 kDa. This is consistent with the scattering from a slightly elongated SarA dimer (calculated MW of 29.4 kDa). Interestingly, in the presence of 10 mM $MgCl_2$, the bimodal analysis of the 11.7 mg/mL SarA solution revealed a monodisperse solution with a macromolecular species of molecular weight 56 kDa. This suggests a divalent metal ion-dependent tetramerization and more globular fold to the tetrameric species. Taking the cross-linking and DLS experiments together, SarA appears to be a stable dimer, which can form tetramers at high protein concentrations and in the presence of Mg. Tetramer formation may be a critical activity in the regulation of agr operons by SarA.

Determination of the Activity of Recombinant SarA

Figure 2:
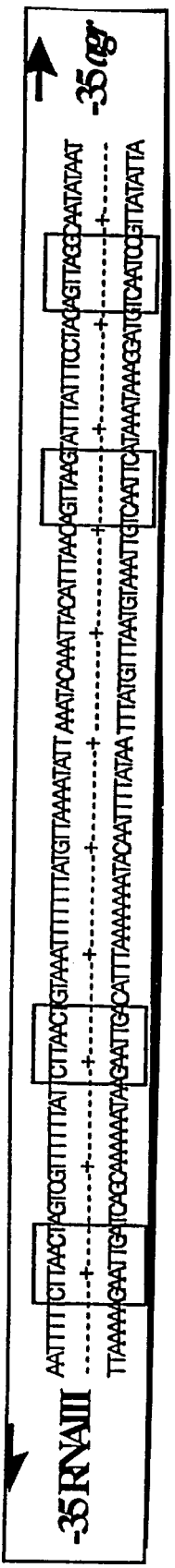
FIG. 2 depicts a sequence of the agr enhancer regions between the P2 and P3 promoter (SEQ ID NOS:8 and 9). The heptad repeats reported by Morfeldt et al. (1996) are shown in the boxes.
Figure 6:
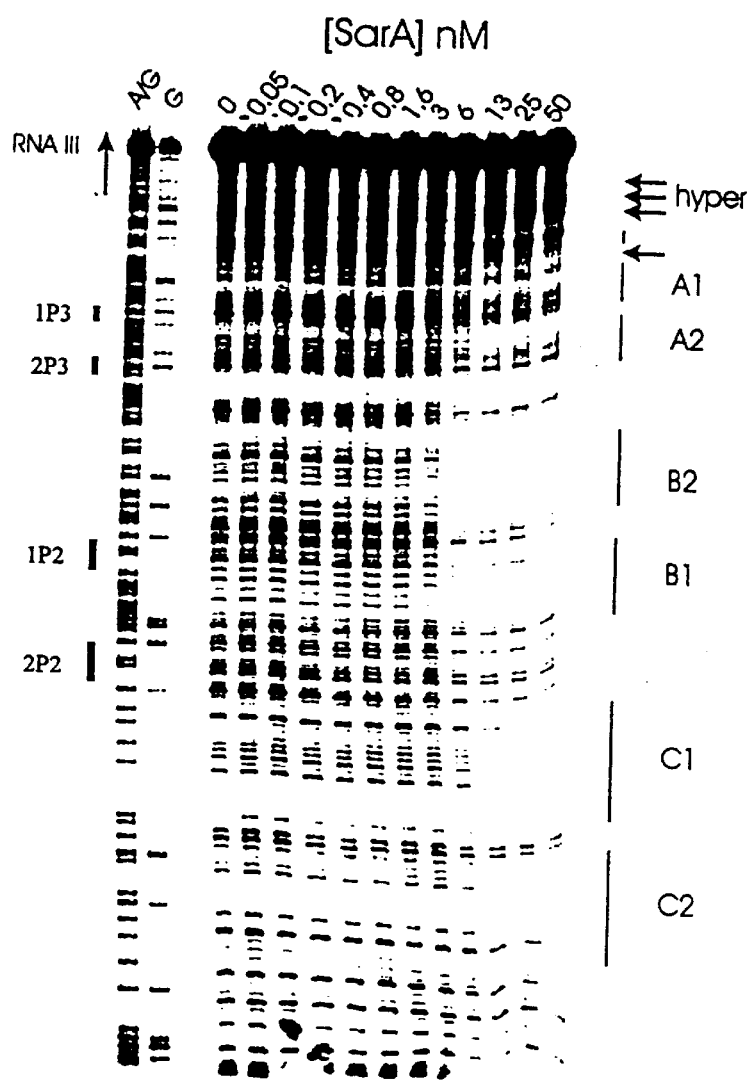
FIG. 6 depicts DNase I protection analysis of Sar A interactions with the P2–P3 promoter region. A, Representative DNase I result. $^{32}$P-labeled DNA fragment was equilibrated with various concentrations of SarA prior to treatment with DNase I. Samples were resolved by denaturing gel electrophoresis and detected by phosphorimaging. A/G, G, chemical sequencing standards, solid bars on left side (e.g., 1P3, 2P3, etc.) indicate the position of the heptad repeats, solid bars on right side e.g., A1, A2, etc.) indicate protected regions, and the arrows indicate hypersensitive sites. B. Alignment and consensus sequence of protected regions (SEQ ID NOS:12–18, respectively).

With the oligomeric state of SarA known to be a dimer and the binding sites further defined by DNase I footprinting, stoichiometric binding analysis was performed to determine how active the E. coli expressed, pure preparation of SarA was and the stoichiometry of SarA-DNA complexes. Using synthetic DNAs (A1/A2 or B1/B2 shown in FIG. 3) as targets in EMSA, it was determined that recombinant SarA is approximately 95% active, which corresponds well with the level of purity observed in SDS-PAGE. These experiments were carried out by titrating a concentration of $^{32}$P-labeled DNA that is 100-fold higher than the apparent $K_D$ with SarA (Riggs et al. 1970; Hurlburt and Yanofsky, 1990). The amount of DNA present in the shifted and unshifted bands was determined by phosphorimaging. The concentration of protein required to shift 50% of the DNA was used to determine the stoichiometry and activity from the equation: $K_D=[\text{SarA}]_{1/2}-\frac{1}{2}[\text{DNA}]$ which is derived from the equilibrium expression. Under conditions where the DNA concentration is very high relative to the $K_D$, the equation becomes $[\text{SarA}]_{1/2}=\frac{1}{2}[\text{DNA}]$. Since the concentration of the synthetic DNA fragment is known one can accurately calculate the activity of the DNA-binding protein.
Determination of SarA Secondary Structure Using Circular Dichroism The protein concentration utilized for this study was 1.8 mg/ml in a solution of 50 mM potassium phosphate, pH 7.5. The circular dichroism spectrum was taken from 260 nm to 180 nm. The spectrum showed large negative ellipticity at 208 nm and 220 nm indicative of a high helical content (Rechtin et al., 1999). Using the spectrum from 260 nm to 190 nm, the percentage of each secondary structure element was calculated. The results were: Helix-54.9%, Strands-6.3%, Turns-14.5% and Random coil-26.7%.
DNase I Footprinting of SarA Binding to the Putative agr Regulatory Region Based on the work of Morfeldt et al. (1996), the 130 bp that span the −35 regions of the P2 and P3 promoters of the genes of the agr locus contain target binding sites for SarA (FIG. 2). This work further indicates that a DNA fragment containing 50 bp upstream of P3, in the context of the intact RNAIII gene is sufficient for appropriate, Sar-mediated expression of RNAIII in S. aureus. The four heptad repeats (indicated in FIG. 2) divergently arranged within the 130 bp region were considered to be important and that notion was supported by qualitative EMSA data in that work. To test this notion and identify binding sites for SarA in this region, DNase I footprinting was perfomred with the purified SarA. The target DNA for DNase I footprinting was a fragment of plasmid pBKH50, which contains the P2 promoter, the P3 promoter and the intervening DNA. $^{32}$P-end-labeled DNA templates (40 pM) were titrated with DNase I to establish the conditions for one cleavage per molecule, then those conditions were used with a series of SarA concentrations. The data were quantified by phosphorimaging. A representative DNase I footprinting gel is shown in FIG. 6A. The other strand of DNA was labeled and used in footprinting experiments, showing essentially the same results (data not shown). From this analysis, protected regions are obvious at very low concentrations of SarA (marked A1, A2, B1, B2, C1 and C2 in FIG. 6A). The footprinted regions were protected by more than 50% in the presence of 3–6 pM SarA and do not correspond to the divergent heptad repeats cis to the two promoters. Thus, the interactions of SarA with this DNA are of very high affinity, an observation that is confirmed by the EMSA data (below). Furthermore, using EMSA under stoichiometric conditions, it is shown that each pair of footprints is bound by one SarA dimer and that the entire region is bound by three SarAs (data not shown). The sequences of the footprinted regions were aligned and a consensus derived using programs resident in the GCG software package (FIG. 6B). A summary of these data is presented in FIG. 3. The bold boxes indicate the footprinted regions, which are of uniform size and spacing of half sites. It should be noted that the A1/A2 site lies completely within a DNA fragment shown by Morfeldt et al. (1996) (see FIG. 2) to be sufficient for SarA-mediated regulation of RNAIII expression (pEX085, see FIG. 3). DNA sequences with high homology have also been identified downstream of the P3 promoter in the RNAIII gene.

Figure 7:
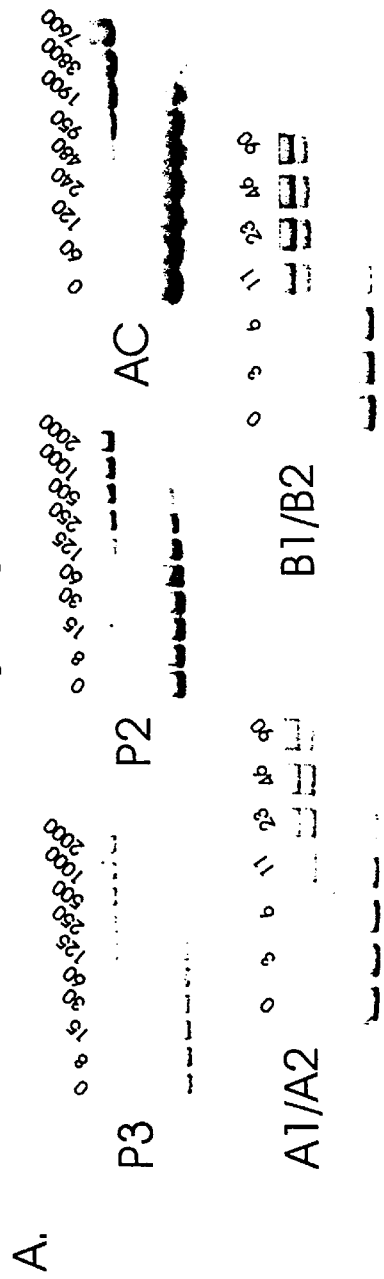
FIG. 7 depicts the quantitative analysis of Sar A binding to regions within the P2–P3 promoter by EMSA. (A) Representative EMSA of SarA and various DNA fragments used in this study. $^{32}$P-labeled DNA fragments were equilibrated with purified SarA, resolved by native PAGE and detected by phosphorimaging. The DNA fragments used are indicated to left side of the data. B. Binding isotherms of EMSA data from A. The concentration of bound DNA was calculated and plotted versus the concentration of SarA present in the sample. DNA fragments used: P3(▲), P2(■), AC(●), A1/A2(♦), B1/B2(▼).
Figure 7:
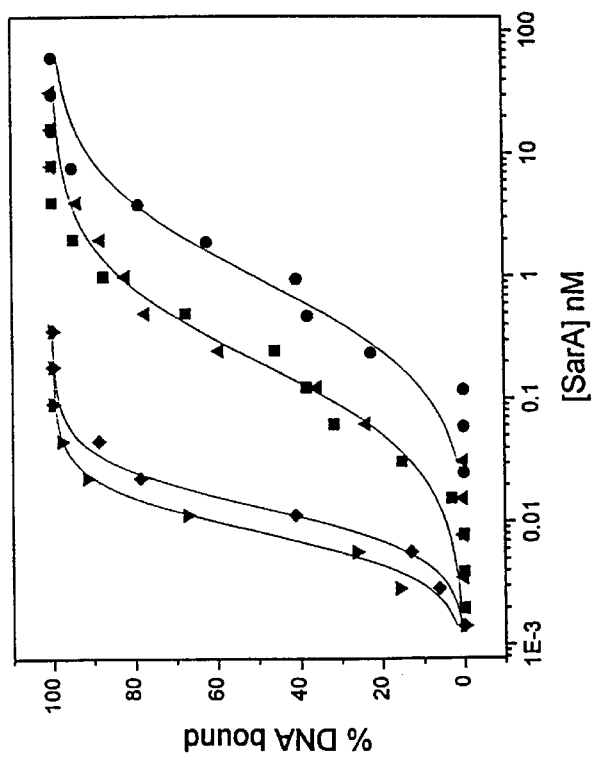
Figure 8:
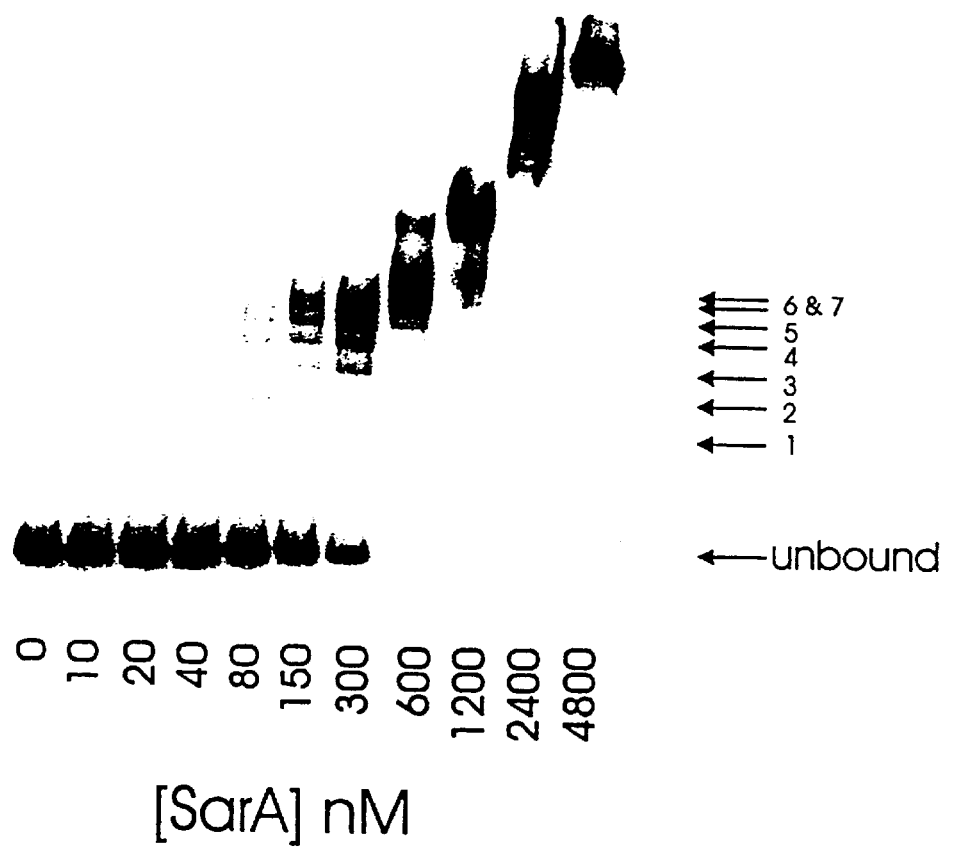
FIG. 8 depcits EMSA of SarA with entire agr enchancer fragment under stoichiometric binding conditions.

Specifically, the conditions for performing the DnaseI footprinting methods are disclosed in Rechtin et al. (1999), which is herein incorporated by reference in its entirety. Briefly, the region of DNA (shown in FIG. 3) was cloned from the genomic DNA of the S. aureus strain DB by PCR amplification. The primers contained BamHI sites and the PCR product was cloned into the BamHI site of the plasmid, pUC118, to form pBKH50. A 240 bp DNA fragment containing the P2–P3 promoter region was PCR amplified from the plasmid pBKH50 with the $^{32}$P-end-labeled primers, −40 and M13 reverse. SarA was allowed to bind to the DNA in a reaction mixture containing 40 pM of $^{32}$P-labeled DNA, 10 mM Hepes (pH 7.6), 5 mM $MgCl_2$, 1 mM $CaCl_2$, 1 mM DTT, and 100 mM KCl at room temperature for 30 minutes. An amount of DNase I, which produced approximately 50% non-nicked DNA, was added to the reaction mixture and incubated for 2 minutes. The reaction was quenched by addition of stop solution (80% EtOH, tRNA (1 ug/ml), 0.3 M $NH_4OAc$) and immediately put into a dry ice/EtOH bath for 30 minutes. A visible pellet was obtained after centrifugation and washed with 70% ethanol. Following denaturing gel electrophoresis, the DNA fragments were detected and quantified by phosphoimaging. The radioactivity in the bands for samples containing SarA was subtracted from the no protein control using Microsoft Excel. The concentration of SarA required to protect a cleavage site fully was determined. To identify the regions of protection within the inter-promoter region, purine sequencing was included in the analysis. Chemical sequencing was done according to standard procedures.
Determination of the $K_D$ Values for SarA and Putative Binding Sites To determine the affinity of SarA for the putative binding sites, quantitative EMSA was performed with synthetic DNA fragments shown in FIG. 3 (A1/A2, B1/B2, P2, P3 and AC). A1/A2 and B1/B2 were identified in DNase I footprinting experiments (Rechtin et al, 1999). P2 and P3 were proposed by Morfeldt et al. (1996) and AC was proposed by Chien and Cheung (1998). In the latter publication, the AC fragment was used to test the importance of the footprint reported. The oligonucleotides were synthesized, end-labelled with $^{32}$P and purified after denaturing polyacrylamide gel electrophoresis (PAGE). Complimentary DNAs were annelaed, purified by native gel electrophoresis and used in the binding experiments. Quantitative EMSA was performed with these synthetic DNA fragments to determine both the stoichiometry of SarA binding and equilibrium dissociation constants ($K_D$). DNA concentrations greater than 10 nM were used for stoichiometric binding analysis. For experiments determining $K_D$ values, concentration of labeled DNA used was extremely low (<10 pM). Various concentrations of SarA were incubated in a 20 μl reaction buffer with $^{32}$P-labeled DNA and in buffer containing 10 mM HEPES, pH7.6, 1 mM EDTA, 2 mM DTT, 50 mM KCl, 0.05% Triton X-100 and 5%glycerol. Binding reactions were allowed to equilibrate for 30 minutes before electrophoresis. Bound products were separated from free DNA on 6% native polyacrylamide (50:1 acrylamide-bisacrylamide) in 0.5×Tris borate-EDTA. Gels were run at 200 V, and temperature was maintained at 16° C. with a circulating water bath. Resolved gels were dried and the products quantified by phosphorimaging. The amount of bound DNA was calculated from the reduction in the unbound DNA and plotted against the respective SarA concentrations. A limiting amount of $^{32}$P-labeled DNA was titrated with SarA, displayed on native gels and quantified by phosphorimaging. Under these conditions, the equation $K_D=[SarA]_{1/2}-\frac{1}{2}[DNA]$ simplifies to $K_D=[SarA]_{1/2}$, where the $K_D$ is equal to the concentration of SarA required for 50% complex formation. In addition, the data were fit and $\Delta G$ values derived using the biological equation solver, BIOEQS (Royer et al., 1990; Royer and Beechem, 1992; Royer, 1993). Representative autoradiograms and the derived binding isotherms are shown in FIGS. 7A and 7B, respectively, and the data are summarized in Table I, below. The DNAs corresponding to footprints A1/A2 and B1/B2 were bound with the highest affinity ($K_D$=7–10 pM). The P2 and P3 DNAs were bound with significantly lower affinity ($K_D$=200 pM) and an oligo corresponding to the region revealed by Chien and Cheung (1998) was bound with relatively low affinity ($K_D$=1 nM). The affinity of SarA binding these DNAs correlated with the number of half sites present. A1/A2 and B1/B2 have two intact half sites. P2 and P3 have 1.5 half sites and AC has one half site. Each DNA fragment was tested by stoichiometric EMSA and found to be bound 1:1 by SarA (data not shown).

may result in the band indicated by 1 in FIG. 8, whereas SarA bound to the B1/B2 site may yield band 2, etc. The different mobilities would result from subtle differences in the DNA conformation when SarA is bound at different sites. This interpretation is reasonable since the binding sites are observed in DNase I footprinting analysis at low concentrations of SarA. In addition, electrophoretic mobility changes resulting from conformational changes in protein-DNA complexes are well established (reviewed in Lane et al., 1992). Furthermore, quantitative analysis of the data indicates that there is no dramatic positive cooperativity to the tandem binding events. The results of our EMSA with small DNA fragments shown in FIG. 7 also indicate multiple SarA-DNA complexes, but only when two intact half sites are present. It is believed that SarA binds to two half sites and can alter that conformation of the DNA between those sites.

Crystallization and Preliminary Structural Characterization of *S. aureus* SarA

Data-quality crystals of SarA have been grown by the vapor diffusion method in hanging drops (McPherson, 1990). Specifically, SarA was concentrated to 20 mg/mL in 20 mM Tris-HCl, pH 7.5, 150 mM NaCl, 1 mM DTT and 1 mM EDTA and mixed 1:1 (v:v) with the crystallization reagent (5% isopropanol, 10 mM $MgCl_2$, 50 mM Tris-HCl pH 7.6). This solution is then equilibrated over a 1 ml

TABLE I

Summary of Binding Constants

| oligo | size | half-sites | $\Delta G$ of dissociation (kcal/mole) | $K_D{}^a$ | protein:DNA* |
|---|---|---|---|---|---|
| P3 | 45 | 1.5 | 13.0 | 220 pM (1.0) | 1:1 |
| P2 | 45 | 1.5 | 13.0 | 220 pM (1.0) | 1:1 |
| AC | 45 | 1.0 | 12.1 | 1 nM (1.0) | 1:1 |
| A1/A2 | 59 | 2.0 | 14.8 | 10 pM (2.0) | 1:1 |
| B1/B2 | 59 | 2.0 | 15.0 | 7 pM (2.0) | 1:1 |

$^a$Number in parentheses represents cooperativity values, p values, from analysis of binding curves
*Ratio of SarA dimer per mole of DNA Interaction of SarA with the Entire P2–P3 Region From the DNase I footprinting and EMSA results, it is clear that SarA binds multiply to the entire agr enhancer region. EMSA presented in Morfeldt et al. (1996) showed a ladder pattern when the entire region was used as a target which indicates multiple protein binding. Since those data were produced with *S. aureus* extracts, the present invention tested the recombinant SarA for this activity. FIG. 8 shows a representative EMSA of a DNA fragment corresponding to the entire agr enhancer region performed under stoichiometric binding conditions (200 pM). The same ladder pattern is evident. The simplest interpretation of these data is that an increasing number SarA proteins are binding to the DNA fragment and causing the increased retardation of the complexes in EMSA. In other words, SarA first binds to the highest affinity sites and the resultant shifted DNA is indicated by 1 in FIG. 8. Increasing the SarA concentration results in additional dimers binding until the entire region is saturated. This simple interpretation leads to the conclusion that greater than 9 SarA dimers are binding this large fragment of DNA. However, since the ratio of SarA to DNA is 3:1 at the lowest concentration of protein required to completely shift all of the DNA, we consider that conclusion to be highly unlikely. Rather, it is believed that some of the bands shown in FIG. 8 result from conformers with the same stoichiometry. In other words, SarA bound to the A1/A2 site reservoir of the crystallization reagent at 4° C. The initial volume of the crystallization drop is 20 μL. SarA crystals grow relatively slowly, appearing after two weeks. The crystals can continue their growth for an additional 2 months. To date, the largest measured crystal dimensions are 0.7 mm×0.2 mm×0.05 mm.

Crystallography

Figures 9, 10:
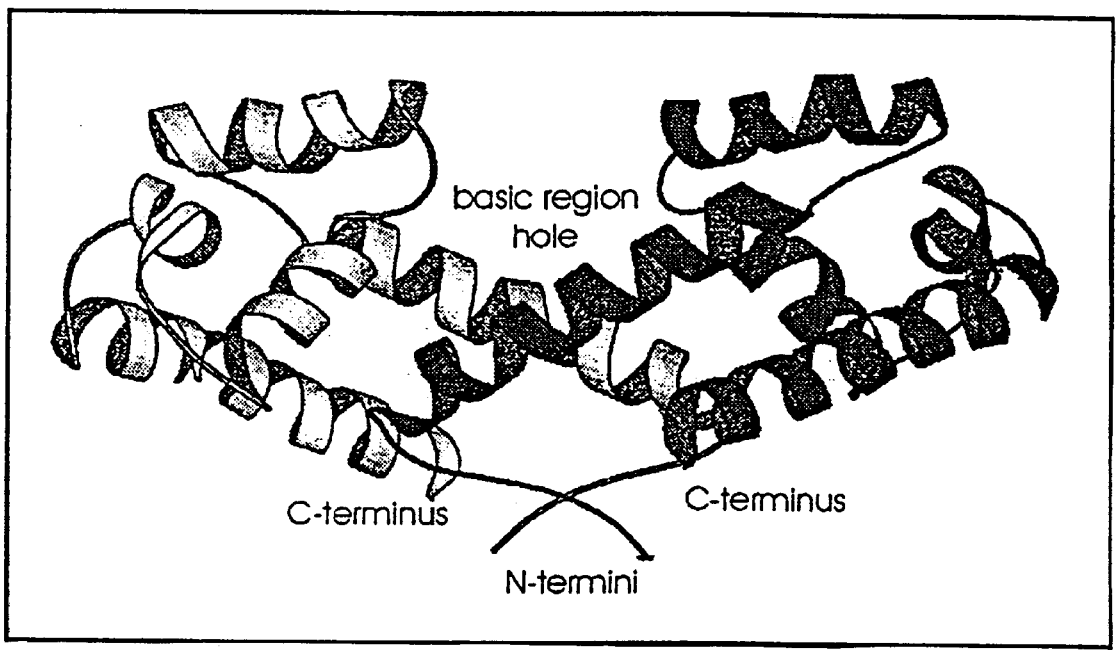
FIG. 9 depicts the initial structure of SarA. Helix 1 (residues 10–30) is very basic and likely represents the DNA-binding domain.
FIG. 10 depicts the summary of helical arrangement of SarA from preliminary structure (SEQ ID NO:19). The missense and nonsense changes in RN6390 are also indicated.

Small angle (5°) precession photography of the hk0 and 0k1 zones reveals the mmm symmetry of the crystal and the presence of three $2_1$ screw axes (later confirmed by intensity data collection). Analysis of these photographs yield unit cell dimensions of a=89.2 Å, b=145.7 Å, c=45.8 Å and $\alpha=\beta=\gamma=90°$. The space group is $P2_12_12_1$. With 4 equivalent positions per unit cell, it is likely that there is a tetramer of SarA in the asymmetric unit. The $V_M$ is 2.4 Å$^3$/Da. A high resolution data set for this SarA crystal form (1.7 Å) was collected at the Stanford Synchrotron Radiation Source. A preliminary structure of SarA α carbon backbone is shown in FIG. 9. SarA is completely α-helical, as expected from the circular dichroism data (summarized in FIG. 10). The first helices are the likely DNA-binding domains. This notion is based on a high density of basic amino acids in the C-terminal half of helix 1 (K21, K23, K27 and K28) and electron density being visible in this region in the crystals of the SarA-DNA complexes. To accommodate binding two segments of DNA that are separated by two turns of the DNA helix, the DNA must not simply lie in the basic region hole (perpendicular to the plane of the page). Rather it is more likely that helix 1 from each subunit lies in the major groove of the binding sites and the DNA is more parallel to the plane of the page. The DNA between the mapped binding sites must be severely bent in order to return to the protein and interact with the N-terminal helix of the other subunit. It should be noted that this structure is not homologous to any previously described transcription factor.

Crystallization and Preliminary Structural Characterization of *S. aureus* SarA-DNA Complex Initial attempts to obtain SarA-DNA co-crystals utilized oligonucleotides based on the heptad repeats reported by Morfeldt et al. (1996). Several DNAs were used in the attempts, ranging from 7–21 bp in length. Data quality crystals were grown that diffract to 2.5 angstroms. The crystals take the space group $P2_1$, with a=54.5 Å, b=65.2 Å, c=57.8 Å and β=118.0°. An initial three dimensional x-ray intensity data set has been collected from a small crystal (smallest physical dimension <0.02 mm) with an R-Axis IV imaging plate area detector at ambient temperature (18° C.). X-rays were generated using a Rigaku RU-300 rotating anode x-ray generator, which equipped with Yale focusing mirrors, set at 50 kV, 100 mA. An automatic indexing routine confirmed the cell constants as calculated from small angle precession photographs. Intensity data were processed with Biotex (MSC, Woodlands, Tex.). Although diffraction was observed beyond 2.7 Å, the data were processed conservatively because of the rapid x-ray induced crystal decay. The $R_{Merge}$* for data in the 30.0 Å to 3.0 Å resolution range (41,345 observations) was 8.2% for all reflections, 7.6% for full reflections, and 9.2% for partial reflections. The final merged file contains 7,157 unique reflections and is 75% complete. (*$R_{Merge}=100\times(\Sigma I_{ave}-I_0/\Sigma I_{ave})$).

Figure 11:
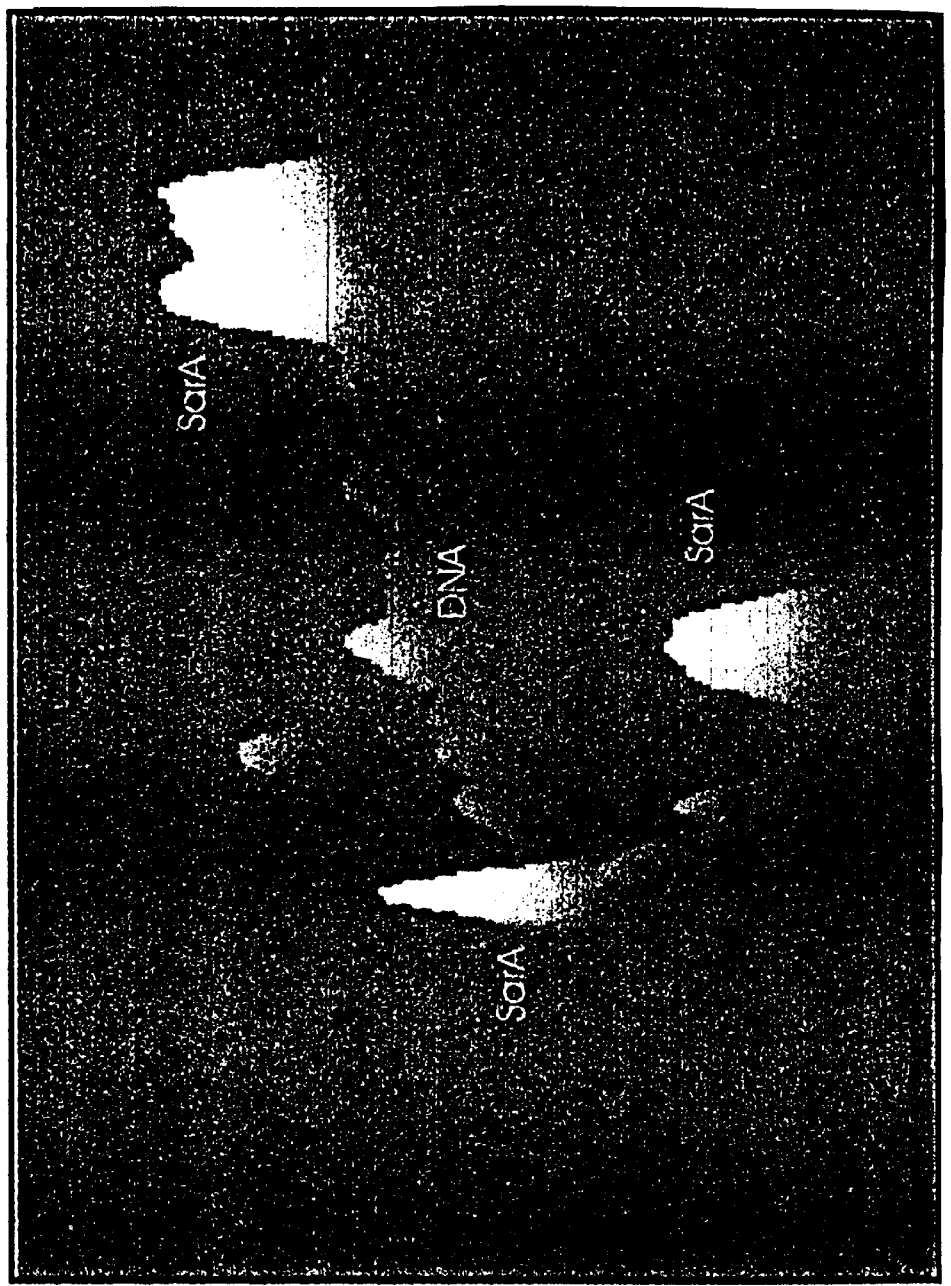
FIG. 11 depicts the atomic force microscopic (ATM) image of SarA bound to DNA. The DNA fragment includes the P2 and P3 promoters and the approximately 250 bp of RNAIII gene.

Visualization of SarA Complexes with the agr Region Using Atomic Force Microscopy To establish conditions for observing SarA-DNA complexes directly, AFM was used with samples of SarA and a 400 bp DNA fragment containing the P2 promoter, the P3 promoter and most of the RNAIII gene. This DNA fragment contains all of the SarA binding sites identified by DNase I footprinting and from sequence analysis of the RNAIII gene. Briefly, a mixture of 10 nM SarA and 1 nM DNA fragment in 10 mM NaPO$_4$ pH 7.4, 50 mM KCl, 10 mM MgCl$_2$ was deposited on a freshly cleaved mica disk (1 cm diameter), washed with water and dried for 20' prior to imaging. A Nanoscope III microscope in tapping mode was used to image the molecules on the surface of the mica at 1.798 volts, at a scan rate of 2.035 Hz. The image shown in FIG. 11 is representative of other complexes present on the surface. It appears that SarA binds to at least 3–4 positions in the DNA fragment, at both ends, and approximately ⅓ of the way from one end. The largest complex (top right) may represent tandemly bound SarA dimers. The simplest interpretation of this data is that the SarA-DNA complex at the bottom of the image is cis to the P2 promoter (C1/C2 site), the Sar-DNA complex ⅓ of the length of the fragment in is cis to the P3 promoter (A1/A2 site) and the large SarA DNA complex at the upper right is within RNAIII. It is not clear if the B1/B2 site was occupied in this image.

Working Model for SarA Regulation of the Genes in the agr Locus

Figure 12:
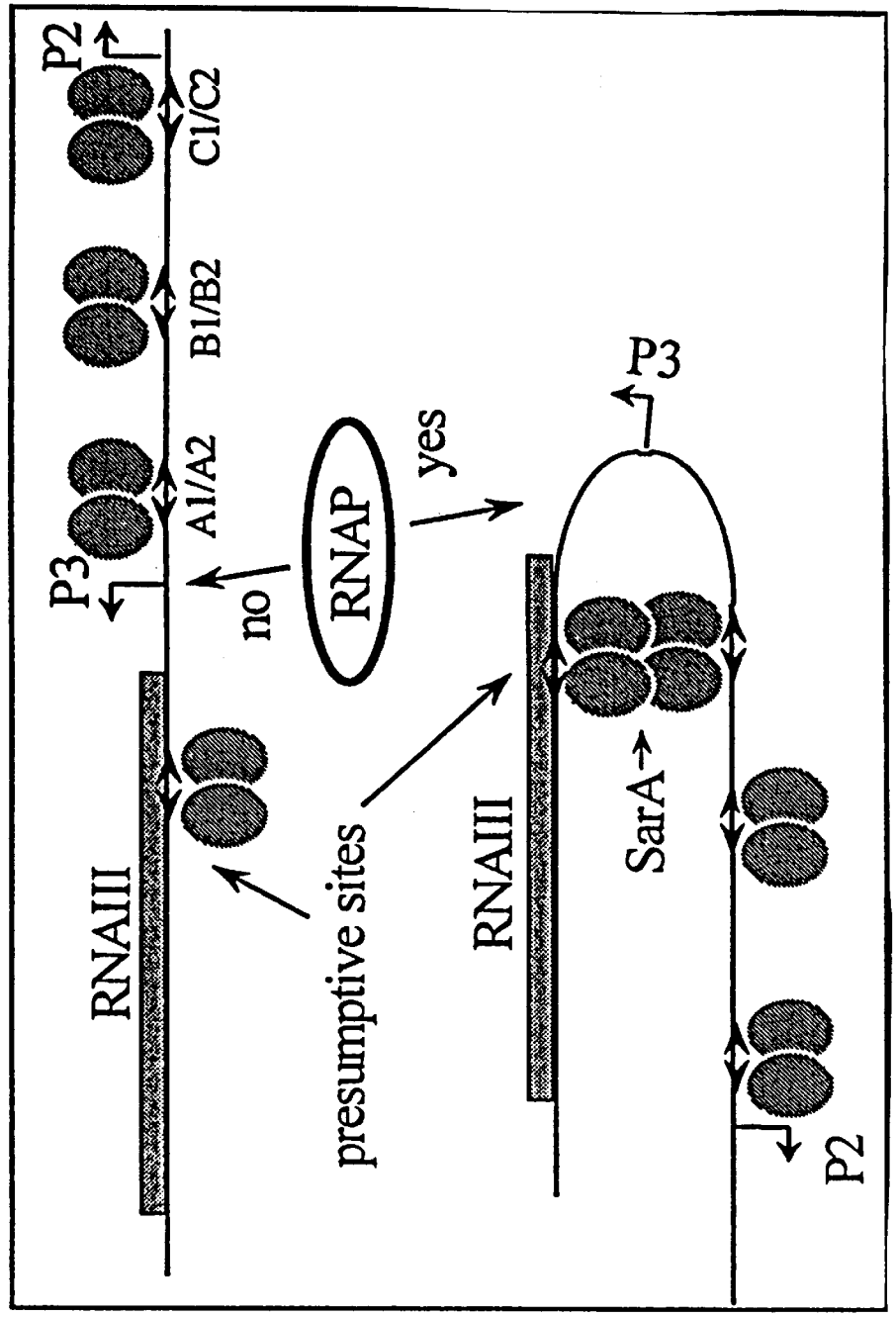
FIG. 12 depicts a proposed model of SarA-induced superhelical activation of P3 promoter. SarA is shown as a dimer that can bind to the A, B, and C sites identified by Dnase I, as well as to a presumer site downstream of P3. By a mechanism that is not understood, SarA activates the promoter, perhaps by tetramerization, in response to quorum establishment.

Based on the data obtained and reports from other studies, a working model of SarA-agr interactions was generated. In the model, SarA binds to DNA and increases the superhelical turns of nearby promoter DNA (schematically depicted in FIG. 12). In the case of agr, this activates expression. Implicit in this model are the presence of SarA binding sites downstream of the regulated promoter as well as upstream. These sites are predicted by sequence analysis and tentatively observed in the AFM study. In the working model, dimeric SarA binds to a DNA target upstream of P3 and another dimer binds downstream of P3. The dimers would associate to form tetramers by an presently unknown mechanism (e.g., post-translational modification or small molecule effectors). The intervening DNA is topologically altered, specifically, it is over-wound. Over-winding would place the −35 and −10 regions of the P3 promoter closer together and allow higher affinity binding by RNA polymerase.

The following observations are accounted for by this model:

1. 50 bp upstream of P3 is necessary for SarA-mediated regulation of RNAIII (pEX085 in FIG. 7 above, and Morfeldt et al., 1996). SarA is a dimer, which binds to the 50 bp DNA fragment containing the A1/A2 site. SarA dimers can associate and form tetramers under appropriate conditions (Schumacher, Hurlburt and Brennan, unpublished).
2. the −10 and −35 regions of the P3 promoter are 3 bp too far apart for highly efficient binding by RNA polymerase.
3. deletion of 3 bp from the P3 promoter results in constitutive, SarA-independent expression (Morfeldt et al., 1996).
4. There are regions downstream of the P3 (and P2 promoters) that are homologous to the highest affinity SarA binding sites (the present invention) and preliminary AFM shows SarA binding downstream of P3 (the present invention).
5. SarA is expressed constitutively throughout the exponential growth phase and into post-exponetial stages (Blevins et al., 1999).
6. SarA, expressed in *E. coli* (unmodified or un-affected by small molecule effectors) can bind DNA sites with very high affinity (Rechtin et al, 1999).
7. Although not widespread, precedents exist for superhelical control of promoter activity (e.g., MerR of *E. coli*, Ansari et al., 1992; Ansari et al., 1995).
8. Commensurate with activation of agr genes, SarA represses the collagen adhesin gene (cna; Gillaspy et al., 1998; Blevins et al., 1999). The cna promoter has perfect spacing between the −10 and −35 regions. Binding of SarA and subsequent overwinding of the cna promoter would reducethe affinity of RNAP and reduce expression. MerR can act either as a repressor and an activator, dependent on its induced DNA topology changes (Ansari et al., 1995).

Homology of SarA and agr Regions in Clinical Isolates

The present invention is based on the determination of the mechanism of SarA regulation of the two operons in the agr locus and developing inhibitors of that regulation. Based on the strain-to-strain variation observed by Novick and colleagues (Ji et al., 1997), it was a concern that the inhibitors would not work on all clinically-relevant strains. To address this issue, the SarA structural gene and agr enhancer region from thirty genetically distinct strains of *Staphylococcus aureus,* most of which are clinical isolates, were cloned and sequenced (Smeltzer et al., 1996; Smeltzer et al., 1997). Briefly, the regions of interest were amplified by PCR and cloned into the pTOPO-CR2.1 vector. Several independent clones were sequenced (both strands) from each strain and compared to strain DB for differences. With regard to the SarA coding region, the only changes were observed in strain RN6390: all of the clinical isolates were identical to DB. The agr enhancer region was identical in all strains tested. This result is very important as it supports the utility of the present method of treatment against a broad scope of staphylococcal strains and supports the effectiveness of an inhibitor of SarA in the clinical setting.

Summary of Experiments Studying the Nature of the SarA Binding Site in the agr Region The interaction of purified SarA with the DNA region between the divergent promoters for the agr operons, P2 and P3 was biochemically characterized. In DNase I analysis, three sets of SarA-dependent footprints were detected with the highest affinity sites, B1 and B2, in the inter-promoter region more proximal to the P2 promoter. Two pairs of footprints with slightly lower affinity for SarA, A and C, that overlapped to the −35 positions of the P2 and P3 promoters were also observed. Determination of binding stoichiometry by EMSA of the entire inter-promoter region revealed a SarA:DNA ratio of 3:1, indicating that each pair of binding sites was comprised of two half-sites. It is interesting to note that the half sites are two turns of the DNA helix apart, in contrast with the binding sites for many other well-studied prokaryotic regulatory proteins, e.g., trp repressor, λ repressor, cro, lac repressor, which are one turn of the helix apart. The binding sites determined by our DNase I footprinting do not overlap all the heptad repeated sequences observed by Morfeldt et al. (1996). However, the A1 and A2 sequences are within the construct pEX085, which were reported to contain the minimal sequence required for SarA-dependent transcription of RNAIII (see FIG. 3). These results do not concur completely with Chien and Cheung (1998). The discrepancies between these results and those of Cheung's group can most easily be explained by the nature of the recombinant SarA protein. Whereas, the characterized SarA is expressed as a full-length, unmodified form, Cheng's SarA was expressed as a N-terminal GST fusion. It has been determined that the N-terminus is very sensitive to modifications.

Quantitative EMSA was used to test the affinities and stoichiometry of SarA for the sites described above, as well as sites proposed by others using synthetic DNA fragments. The $K_D$ values derived from analysis of the results show SarA binding affinity was the highest for DNAs containing intact binding sites and decreased when only partial sites were present. The stoichiometry of SarA binding to all the DNA fragments we tested was 1:1. The $K_D$ values determined in this study are dramatically lower than those reported by Chien and Cheung (1998). The results presented of SarA interactions with the agr region shows that there is a stable dimer of SarA binding preferentially to three specific sites, each containing two half-sites, upstream of the regulated P2 and P3 promoters. Only one half site (B1) is contained within the DNaseI footprint reported by Chien and Cheung (1998).

Whereas a consensus site was derived from the six half sites, the optimal sequence for a SarA binding site is still not obvious. Identification and characterization of other sites in genes that are directly regulated by SarA, e.g., cna, (Gillaspy et al.,1997; Blevins et al., 1999) will contribute to this knowledge. Significant homology has been observed among sequences cis to genes with altered expression in SarA mutants (e.g., tst, spa, hib, seb, hla) with the binding site described by Chien and Cheung, which contains the B1 half site (Chan and Foster, 1998). However, none of these genes has been shown to be directly regulated by SarA. A common theme among the SarA protected sequences described in the present invention is AT-abundance (79 to 89%).

The multi-band pattern of SarA-DNA complexes observed in EMSA experiments with the larger fragments of DNA are similar using SarA in extracts of *S. aureus* (Morfeldt et al., 1996) and recombinant, purified SarA. These multiple bands are only present when the DNA fragment used in EMSA contains at least two intact half sites. As mentioned above, a simple interpretation of this phenomenon would have different SarA:DNA conformations utilizing different sets of half sites. However, several lines of evidence lead to a more complicated, yet interesting model, namely that SarA induces changes in the superhelicity of the DNA fragment (originally proposed by Morfeldt et al., 1996). First, the spacing between the −10 and −35 regions of the P2 and P3 promoters is approximately 3 bp too far. Deletion of 3 bp from the P3 promoter resulted in constitutive, SarA-independent expression of RNAIII (Morfeldt et al., 1996). Thus, one effect of SarA is to overcome this spacing. Next, the EMSA with the A1/A2 and B1/B2 fragment shows two band shifts occurring simultaneously, although the protein:DNA ratio is 1:1 and only two half sites are present. These two bands might correspond to differences in structure due to SarA binding an AT-rich sequence and changing the DNA conformation. Lastly, the gene encoding the collagen adhesin (cna) is repressed by SarA in late stage cultures, the time when SarA activates the P2 and P3 promoters (Gillaspy et al.,1997; Blevins et al., 1999). The spacing of −10 and −35 regions for the cna promoter is nearly optimal. Thus, SarA binding may serve to over-wind regulated promoters acting as both a repressor and an activator. Precedence for modification of DNA structure has been clearly shown for the MerR protein in *E. coli* (Ansari et al., 1992; Ansari et al., 1995). One requirement of such a model may be that SarA binds downstream of the regulated promoter as well as upstream. There is preliminary data indicating the existence of multiple sites located downstream of the P3 promoter.

Analysis of the cis Regulatory Elements in the agr Locus Responsive to SarA Control As described above, and in conjunction with the work of other groups, good evidence for cis regulatory elements in the region between the P2 and P3 promoters have been provided. Footprinting revealed high affinity binding sites, which were corroborated by quantitative EMSA analysis. In addition, the left half of this region was sufficient for appropriate expression and regulation of RNAIII (Morfeldt et al., 1996). However, several lines of evidence indicate the possible existence of cis regulatory elements downstream of the P3 promoter, in RNAIII (see model above): 1) deletion of three base pairs between the −10 and −35 regions of the P3 promoter yielded Sar-independent, constitutive expression of RNAIII, which suggests topological changes, 2) the EMSA of this invention indicate that major structural changes occur to DNA when it is bound by SarA, 3) sequence analysis has revealed the presence of potential binding sites for SarA downstream of P3, and 4) preliminary AFM shows SarA binding downstream of P3. To affect the topology of the P3 promoter, SarA appears to have binding sites on both sides of the promoter. The existence and significance of these potential sites and the cis elements already identified upstream of P3 are examined by the use of a combination of footprinting, mutagenesis, in vivo expression and in vitro binding assays. Furthermore, DNA fragments carrying mutations in the SarA binding sites and atomic force microscopy are useful to observe changes in the binding patterns directly.

Figure 13:
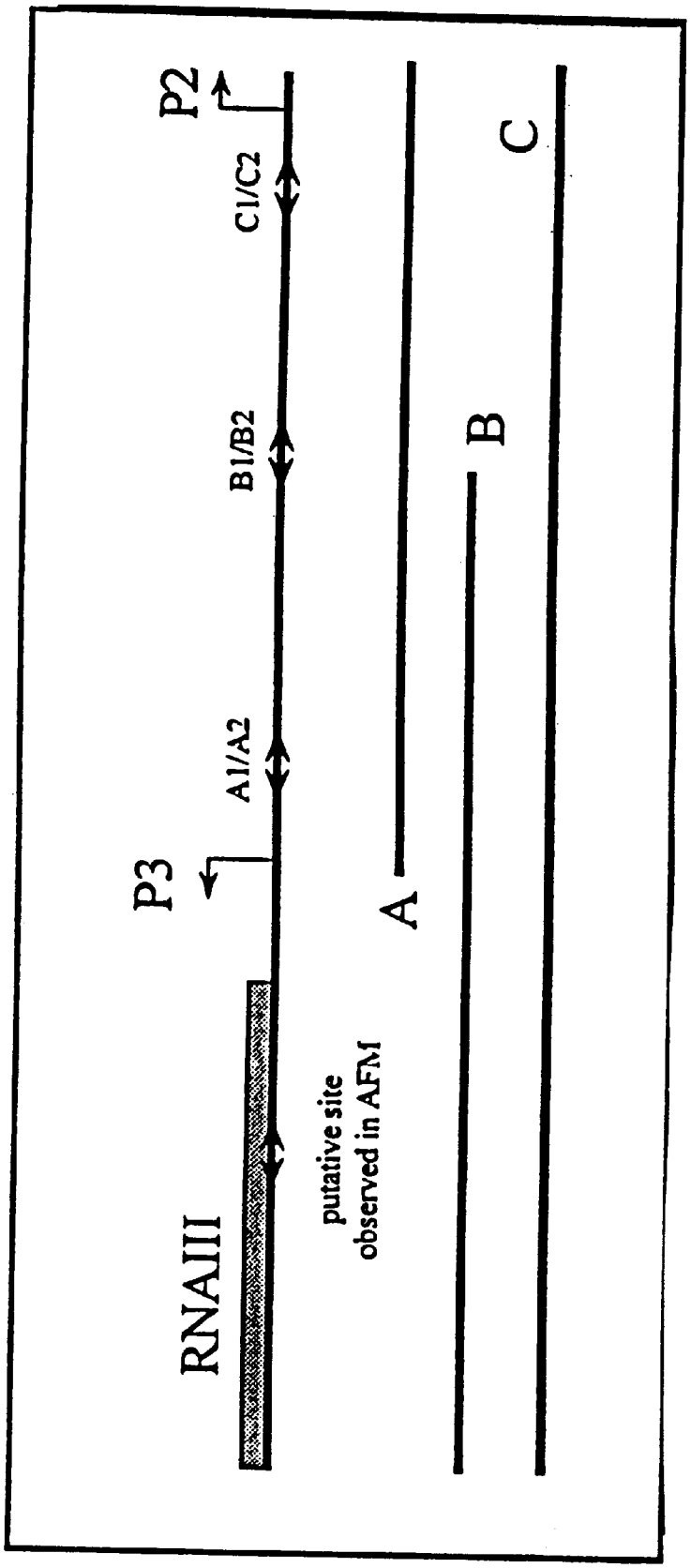
FIG. 13 depicts the agr locus and DNA fragments for study. The binding sites determined by Dnase I footprinting are indicated.

In FIG. 13 the P2/P3 region is depicted. Previously presented DNase I footprinting experiments focused on the region between the P2 and P3 promoters (DNA fragment A in FIG. 13). The footprinting analysis on a DNA fragment containing both the upstream and putative downstream binding sites (Fragment B, FIG. 13) is used to test the possibility of SarA binding sites existing downstream of P3. The DNA fragment (B) is amplified from plasmid pT7B-agr12, which contains the entire RNAIII gene and upstream region to P2 (depicted as fragment C in FIG. 13). The DNase I footprinting is performed exactly as it was done for fragment A (Rechtin et al, 1999). Briefly, one oligonucleotide primer is labeled with $^{32}P$ using polynucleotide kinase and gel purified. This primer and its unlabeled "opposite" primer are used in limited PCR (ca. 20 cycles) with the fragment B clone to generate the end-labeled target DNA for footprinting. The concentration of DNase I required for 1 cleavage/DNA fragment is determined empirically and various concentrations of SarA are added and footprinting assays performed. The samples are resolved on sequencing gels, dried and quantified by phosphorimaging. Radioactive traces of the SarA-containing lanes are digitally subtracted from that in the control (no SarA) lane using Excel (Microsoft). The concentration of SarA required for a 50% diminution of DNase I cleavage is determined. The footprinting technique for SarA already has been optimized as disclosed in Rechtin et al, 1999.

The presence of SarA-dependent footprints downstream of P3 shows that the model presented above is correct. The binding sites that have already been identified (A1/A2, B1/B2 or C1/C2 in FIG. 3 (SEQ ID NOS:10 AND 11)) may be sufficient for SarA-mediated regulation alone. It is important to remember that the experiments described by Morfeldt et al. (1996) showing that a DNA fragment approximately 50 bp upstream of P3 promoter was sufficient for appropriate expression and regulation, contained an intact RNAIII gene. To test if only the upstream DNA is critical, a reporter gene fusion (xylE) to the P3 promoter is made and tested in *S. aureus*.

Putative cis-acting regulatory elements are tested by mutagenesis and northern blot analysis. Plasmid pT7B-agr12 (described above) is used as the template for mutagenesis studies. Briefly, the putative SarA binding sites identified by our previous DNase I footprinting studies, as well as other putative binding sites identified from the footprinting experiments described above are tested. Mutations from A→T and T→A or C→G, G→C (to not affect GC content) are made in the putative binding sites. Initially, 2–3 changes are introduced per experiment in order to be confident that the site has been disrupted. Synthetic oligonucleotides with the desired changed were synthesized and used to prime second strand synthesis of a single stranded DNA template. Recovery of mutants is enhanced by using the thiol-nucleotide system for the mutagenesis (Amersham) (e.g., Mackintosh et al., 1998). The fidelity of the mutants are determined by sequence analysis. Mutants in pT7B-agr12 are used directly for DNase I footprinting. Mutants for expression in *S. aureus* are cloned into vector pCL84. Following electroporation into *E. coli*, transformants are selected on tryptic soy agar containing spectinomycin (50 μg/ml). Testing by DNase I footprinting is accomplished as described above.

To test the effect of altering genetic elements cis to P3, pCL84 clones carrying different mutants are purified from *E. coli* and integrated into the chromosome of *S. aureus* strain CYL316. CYL316 is an RN4220 strain that contains a plasmid (pUL112Δ19) carrying the phage L54a integrase (int) gene. The presence of the integrase gene guides the integration of pCL84, which includes the L54a att site but cannot replicate in *S. aureus*, into the *S. aureus* lipase (geh) gene. After transformation of CYL316 with different pCL84 clones, integrants are selected on medium containing tetracycline (3 μg/ml) and confirmed by lipase assay (all integrants will be lipase negative) and Southern blot with a geh probe. Lipase production is assessed by plating on J1 agar (Dickinson et al., 1968) and using a quantitative spectrophotometric assay developed by the Co-I (Smeltzer et al., 1992).

After confirmation of CYL316 integrants, each mutant is transduced (see below) into WA400 and an RNAIII/sar double mutant. WA400 is a derivative of *S. aureus* strain 8325-4 in which the region encoding RNAIII has been replaced with a chloramphenicol resistance marker. The use of WA400 eliminated the possibility that RNAIII can be expressed from any source other than the recombinant plasmid introduced into geh. Also, while a direct interaction between SarA and components of the agr regulatory system has not been demonstrated, the use of WA400 (rather than the agr-null mutant RN6911) ensures that any undefined interaction between SarA and proteins encoded within the agrBCDA operon will remain possible. As a negative control, plasmids are introduced into an RNAIII/sar double mutant generated by transducing the chloramphenicol-resistance gene from WA400 into PC1839 (kindly provided by Dr. Simon Foster, University of Sheffield, Sheffield, UK). PC1839 is defined by the insertion of a kanamycin-resistance marker into the sarA gene (Chan and Foster, 1998). Transductions are done using phage Φ11 as previously described (Gillaspy et al., 1998). Transductants are screened by plating on appropriate selective medium (tetracycline in the case of the pCL84 integrants and chloramphenicol in the case of the WA400 RNAIII mutation). After demonstrating the presence of the non-selected markers (e.g. kanamycin in the case of PC1839), transductants are confirmed by lipase assay (see above) and by Southern blot using probes for the geh, sar and agr loci (Blevins et al., 1999).

After each mutant was established in WA400 and in the RNAIII/sar double mutant, the effect of altering genetic elements cis to P3 on the SarA-mediated activation of RNAIII transcription is assessed by Northern blot using probes corresponding to sarA, RNAIII and the polycistronic RNAII message derived from the agrBCDA operon. Northern blots are quantified by phosphoimaging analysis. To ensure that subtle differences were detected, the results are normalized by comparison to the results obtained with a probe for a constitutively expressed 16S ribosomal RNA (Blevins et al., 1999). The WA400 produces the sarA and RNAII transcripts while the RNAIII/sar double mutant did not produce any transcript other than a limited amount of RNAII (the amount of RNAII is limited based on the established role of SarA in agr expression). RNAIII is observed only if a plasmid that includes functional versions of the cis elements required for the SarA-mediated expression of RNAIII was introduced. To ensure that the effects observed are mediated by SarA, the results are interpreted by comparison to the level of expression observed with the same pCL84 clone in the corresponding RNAIII/sar double mutant.

Finally, to confirm that the results of the northern blots are biologically relevant, the expression of a gene that is expressed under the regulatory control of RNAIII: hla, which encodes the *S. aureus* α-toxin is assessed. Production of α-toxin is assessed by northern blot, spectrophotometric hemolysin assays employing rabbit erythrocytes and by western blot employing a polyclonal, α-toxin-specific antiserum (kindly provided by Dr. John Iandolo, University of Oklahoma Health Sciences Center, Oklahoma City, Okla.). Northern blots are done as previously described (Blevins et al., 1999). For quantitative hemolysin assays, supernatants are harvested from cultures at various stages of in vitro growth and standardized based on optical density ($A_{560}$) of the bacterial culture. Standardized supernatants are mixed in microtiter plates with an equal volume of 1% washed rabbit erythrocytes. After a 2 hr incubation at 37° C., unlysed cells are removed by centrifugation and the amount of lysis quantitated by measuring the optical density of the supernatant at 410 nm. If necessary to obtain more quantitative data, dilutions of the standardized supernatant were assayed for comparison. For western blot analysis, standardized supernatants were electrophoresed using 10–20% polyacrylamide gradient gels and then transferred to PVDF membranes as previously described (Blevins et al.). After transfer, blots were developed using the rabbit α-toxin antiserum and the Phototope-HRP western blot detection kit (New England Biolabs, Beverly, Mass.).

The possible synergistic effects of multiple binding sites obtained by this approach are examined by using mutagenesis to combine mutations in individual sites into one DNA fragment. For example, if mutants in the A1/A2 site reduces RNAIII expression by 50% in a sar$^+$ strain and the B1/B2 site reduces it by 30%, these mutations can be combined and retested. Potential results are the observation of a 50% reduction, a 80% reduction or elimination of RNAIII expression.

In wild type strains, RNAIII expression is low in early-log phase and high in late-log phase. In sar$^-$ strains, RNAIII expression is very low at all timepoints. If SarA is binding to the proposed sites, then mutation of those sites should diminish or eliminate SarA-mediated activation of P3 and a diminution of RNAIII by northern blot and of α-toxin by western blot will be observed.

The extent of SarA at the downstream sites identified above, the cooperativity in binding to multiple sites, and the loss of affinity in binding to the mutant sites generated in the section above are studied. These experiments are important with regard to the development of inhibitors of SarA-mediated activation of agr genes. The avidity of SarA binding is important in determining the appropriate concentration and affinity required of potential inhibitors. In addition, the characterization of the mutant sites, both in vivo and in vitro, are important in identifying the important bases that comprise the sites which is also important for the design of inhibitors.

The equilibrium binding constants ($K_D$s) for the various SarA binding sites using EMSA, as described above and in Rechtin et al. (1999) are determined. Briefly, synthetic oligonucleotides corresponding to the sites are synthesized and radiolabeled with 32P. Complementary strands are annealed and gel purified. Limiting (<10 pM) DNA are mixed with serial dilutions of pure SarA and resolved by native gel electrophoresis. The radioactive species are detected and quantified in dried gels by phosphorimaging. Each experiment is performed at least three times and averaged. The percentage of bound DNA is calculated from loss of the unbound DNA in the gel and plotted versus the concentration of SarA present in the sample. The data are fit using BIOEQS and Origin, as described in Rechtin et al. (1999). The concentration of SarA that results in 50% bound DNA is equal to the $K_D$ under these conditions (Hurlburt and Yanofsky, 1990; Czernik et al., 1996). A description of the derivation of the equation used to derive $K_D$ is presented above. The relative affinity of the various SarA binding sites reveal the most important ones and corroborate the mutagenesis and expression studies described above. Furthermore, if binding sites are within 20–30 bp of each other, there is reason to suspect that there may be cooperative interactions that may enhance the apparent activity of SarA. This hypothesis is tested by performing EMSA with DNA fragments containing two or more wild type sequences, as well as combination of wild type and mutant sequences. Numerous transcription factors in prokaryotes and eukaryotes utilize cooperativity to affect gene regulation. These experiments reveal such interactions for SarA.

Based on the quantitative EMSA work with oligos described above and in Rechtin et al. (1999), very high affinity binding, with $K_D$ values in the range of 5–50 pM are anticipated. Subtle changes in the sequences flanking the binding sites may also have effects on the affinity of SarA binding. Cooperative interactions between SarA dimers bound to nearby sites are easily recognized by the slope of the binding isotherms. The power logistic fitting function normally used in binding data analysis renders a value ρ that indicates the slope of the curve (Czernik et al., 1996). ρ values of 1 are non-cooperative, greater than 1 are positively cooperative and of less than 1 are negatively cooperative.

Further Analysis of the Structural Components of SarA Responsible for agr Regulation Structural information is important for the rational design of anti-staphylococcal inhibitors. Towards this end, two types of structural determinations are pursued. The first is the traditional x-ray crystallographic approach. Protein or protein and DNA are brought to high concentration, crystallized and the structures are determined from the pattern of x-ray diffraction. This approach typically yields high quality structures at atomic resolution (2.5–1.5 Å). The present invention has already provided a 1.7 ansgstrom data set for SarA alone and crystals of SarA-DNA that diffract to 2.5 angstroms. The second approach is relatively new in biological structure science, atomic force microscopy or AFM. AFM has been pioneered by Dr. Carlos Bustamante and has made a tremendous impact on the field of transcriptional control in the past few years (reviewed in Bustamante and Rivetti, 1996). In AFM, macromolecular species are visualized on mica surfaces in 3-dimensions. Thus, the binding site for SarA can be observed directly, as well as any conformational changes SarA may induce in the DNA. AFM makes it possible to visualize ternary complexes of SarA, P3 and RNA polymerase.

Data quality crystals have been grown of SarA and a SarA-DNA complex. A preliminary structure of the protein alone has been determined.

As described above, crystals of SarA that diffract to 1.7 Å resolution have been grown and an initial chain trace has been carried out. The structure was solved by Multiple Isomorphous Replacement (MIR) (Drenth, 1994) using a thimerasol derivative and a selenomethionine-substituted protein (LeMaster and Richards, 1985). This initial structure was improved by iterative rounds of restrained least squares refinement using the software package TNT (Tronrud et al., 1987) and model rebuilding with O (Jones et al., 1991). Solvent molecules were added at the final stages of refinement. Upon completion of the refinement, the free R values were calculated using 10% of the structure factors that have been excluded from refinement (Brunger, 1992). This parameter provides a statistical check on the accuracy of the protein model. Additionally, "omit" maps were calculated in which 10% of the structure will be removed systematically and the remaining 90% refined to remove any bias. The omitted electron density maps were inspected on a graphics workstation and any problem areas rebuilt and re-refined. Finally, the stereochemical properties of the final protein structure were assessed with PROCHECK (Laskowski et al., 1993). It should be emphasized here that our current SarA crystal form is excellent and the ensuing refinement of the SarA structure will provide an accurate atomic resolution view of this virulence gene regulator.

The current SarA-DNA crystal form described in the application diffracts to beyond 2.7 Å. However, the diffraction limit of these crystals is volume-dependent and x-ray sensitive. As a first approach to extend their resolution, experiments to "thicken" the thinnest crystal dimension are carried out. Such efforts entail the fine screening of multiple crystallization parameters that include pH, ionic strength, counter ion identity, e.g., chloride versus acetate or sulfate, macromolecule concentration, drop volume, the ratio of protein to oligodeoxynucleotide (mole:mole) and the initial volume-to-volume ratio of protein to crystallization reagent, which changes the kinetics of the crystallization process. The addition of small molecule effectors, including divalent cations or nonionic detergents, are also assayed. Other techniques, such as seeding fresh drops of SarA-Octamer solutions with small micro or mini crystals of the complex or the sitting drop or batch methods of crystallization also are used (McPherson, 1990). Additionally, the x-ray sensitivity of the SarA-Octamer complex is overcome by collecting the x-ray intensity data at −170° C., i.e., cryocooled (Roger, 1994). Proven cryosolvents include isopropanol, glycerol, low molecular weight polyethylene glycols and 2-methyl-2,4-pentanediol. "Scooping" experiments, followed by flash freezing the crystal in liquid nitrogen are used. The quality of the resulting diffraction pattern is assessed using the R-Axis IV imaging plate system. Often the crystal experiencesan unacceptably large increase in its mosaic spread as well as ice rings. However, the determination of the suitable cryoconditions for a number of crystals has been successful. Whether or not a cryosolvent is found for the SarA-Octamer, the current limiting resolution is expected to be extended significantly, perhaps by as much as 0.4 Å, when intensity data is ollected at one of the national synchrotron facilities. Resolution beyond the current limit provides not only a more accurate model of the protein-DNA complex, but also a better view of the water structure of the complex. The role of water in protein-ligand is becoming more appreciated in the biology (Frey et al., 1993; Baker, 1995).

As a parallel approach to the above efforts to improve the resolution of the SarA-Octamer complex crystals, alternative DNA sequences are also screened. A sparse matrix approach is used (Jancarik and Kim, 1991). The crystallization experiments employ the hanging drop, vapor diffusion technique and test a variety of crystallization reagents, limited to alcohols and organic solvents, different molecular weight polyethylene glycols (200 to 20,000), inorganics and mixtures of these compounds. The experiments are carried out at either 4° C. or 18° C., as temperature is an important experimental variable. The initial protein concentration of the SarA dimer is 0.5 mM and 0.5 to 1.0 mM for the DNA site. The molar ratio of the protein to DNA is often an important parameter in complex crystallization and in many successful cocrystallizations, the concentration of DNA is higher and ranges to beyond twice that of the protein (Aggarwal, 1990; Schumacher et al., 1994). Perhaps the most critical variable, which must be tested in any protein-DNA co-crystallization experiment is the length of the oligonucleotide as well as the presence or absence of a 5' or 3' overhanging nucleoside (Jordan et al., 1985; Aggarwal et al., 1988; Schultz et al., 1990). From the results discussed above, the oligonucleotides up to 45 base pairs long from the P2 or P3 promoters that encompass two heptad repeats (CTTAACT) is used.

In a typical crystallization screening experiment a 2 $\mu$L drop of the crystallization reagent is added to a 2 $\mu$L drop of the protein-DNA solution. The 4 $\mu$L mixture is then inverted and sealed over a 1 mL reservoir from which the crystallization reagent was taken. Because the protein-DNA drop has approximately half the ionic strength as the reservoir, water diffuses from the drop until equilibrium is reached with the larger volume reservoir. This brings the protein-DNA drop to beyond supersaturation and results in either macromolecular precipitation or crystallization. The results are monitored by inspection of each drop with a stereoscope. The initial screening process requires over 240 set ups per temperature. If a condition looks promising, e.g., crystalline precipitates, small needles or small three dimensional crystals, finer screens are defined as described above and tested until large three dimensional crystals are grown reproducibly. Again, as a point of emphasis it is very likely that a number of oligonucleotides of different lengths, which are blunt-ended or include 5'-nucleoside overhangs, are tried before dataquality crystals of the SarA-DNA complex are grown.

Initial characterization of new SarA-DNA crystals is done by small angle (5° to 9°) precession photography. The resulting diffraction patterns of the principal zones of the crystal allows the determination of the Laue symmetry, systematic absences, likely space group and the unit cell parameters. Three dimensional x-ray intensity data is collected on the native crystals with either a two detector Area Detector Systems Corporation multiwire area detector or a Rigaku R-Axis IV imaging plate area detector (Molecular Structures Corporation). Collected intensities are processed and converted to structure factors with software provided by ADSC or MSC.

The structure of any SarA-DNA complex is determined, for example, by Molecular Replacement (MR) using the refined 1.7 Å resolution structure of the SarA dimer as the search model. The genetic algorithm-based program EPMR (C. Kissinger, personal communication) is used. An additional approach to solve the SarA-DNA structure is the method of MIR, whereby isomorphous heavy atom derivatives are generated by crystallizing SarA with oligonucleotides that have had a specific thymine replaced by 5-iodouracil. Such 5-iodouracil containing oligonucleotides are easily synthesized and purified. The modified oligonucleotide is then used in crystallization experiments which normally yield crystals. Such crystals provide an excellent heavy atom derivative. An added benefit of 5-iodouracil substitution is that every thymine of the DNA binding site can be changed, thus providing the potential for forming several highly isomorphous heavy atom derivatives.

Difference Patterson functions are calculated for all derivatives and the software packages HEAVY (Terwilliger and Eisenberg, 1983) or Phases-95 (Furey and Swaminathan, 1997) are used to locate and refine all heavy atom sites and finally to determine phases for the protein. If necessary density modification, e.g., solvent leveling, as implemented in Phases-95 are carried out to improve the initial MIR electron density map. Chain tracing of the initial electron density map are done with the graphics program FRODO (Jones, 1985) or O (Jones et al., 1991). The initial structure determined by either MIR or MR, is improved and verified as described above for SarA. Additionally, the structural and stereochemical properties of the DNA is assessed using the program Curves (Lavory and Sklenar, 1988).

The initial structure determination of SarA has removed or mitigated many potential problems typically associated with de novo crystal structure determinations. Specifically, it appears that this high-resolution structure will be successful in the molecular replacement structure determination of the current SarA-Octamer complex. Alternatively, the structure determination method of multiple isomorphous replacement as described in the previously herein is used. If there is a problem where none of the 5-iodouracil containing oligonucleotides yield a good heavy atom derivative, alternatively the structure is solved by using a selenomethionine-substituted protein and multiple wavelength anomalous dispersion techniques (Hendrickson et al., 1990). This is a known method to determine structures and is useful for the SarA-Octamer complex. All that is necessary is the proper data collection procedure at a synchrotron facility. Intensity data collection at a synchrotron facility increases the resolution of the SarA-Octamer complex by perhaps as much as 0.5 Å. A final potential problem is the growth of diffraction-quality crystals of other SarA-DNA complexes, which contain oligonucleotides that describe more fully the in vivo binding of SarA to P2 or P3. These oligonucleotides are on the order of 45 base pairs long, possibly resulting in problemts with their cocrystallization with SarA. The Brennan laboratory has had a great deal of success in obtaining crystals of a number of protein-DNA complexes. A very large number of crystallization experiments using a wide variety of oligonucleotides is useful in the present invention.

Atomic Force Microscopic Imaging of SarA-DNA Interactions and SarA-DNA-RNA Polymerase Interactions Atomic force microscopy (AFM) is a powerful technique for observing macromolecular complexes directly. Using this technique, the following can be observe (or not observe): 1) SarA-SarA interactions if looping is occuring, 2) SarA-RNA polymerase interactions, 3) changes in these interactions that result from using DNA fragments with mutant SarA binding sites.

Individual complexes of SarA with DNA fragments from the agr regulatory region, with and without RNA polymerase, are obtained with a Nanoscope III microscope (Digital Instruments, Santa Barbara, Calif.) operating in tapping mode. RNA polymerase from wild type *S. aureus* strain DB is purified according to the methods described in Deora and Misra (1996). After the identification of SarA binding sites, the mutant DNA fragments are used for AFM. Furthermore, SarA mutant proteins that have altered activities also are used. Mutants that express stable proteins, but are either negative recessive, negative dominant or super-activators could have dramatically different effects when bound to DNA. These properties are be visualized using AFM.

For images in air, silicon nitride tips of type TESP with 125 μm long cantilevers are used, whereas assays in buffer require type NP tips. Samples are prepared by depositing 5 μL of a solution of SarA and DNA in a buffer containing 2–10 mM Mg2+, 50–100 mM KCl, 10 mM Tris buffer, pH 7.5, which are the same as for the images described above, onto freshly cleaved mica. Then the surface is rinsed with water and uranyl acetate rinses is tested, since this proved useful in the deposition of trp repressor/operator complexes (Margeat et al., 1998) In addition, the Mg2+ ions bridge the negatively charged DNA to the negatively charged, freshly cleaved mica surface. The mica chip is then allowed to dry in air for 20 minutes before imaging. For imaging in buffer, a drop of buffer is deposited onto the surface after deposition of the complexes. Mean-square end-to-end distances are determined for a large sample of DNA molecules in absence of protein to ascertain that equilibrium deposition has occurred. In presence of protein, the same measurements are carried out to determine if SarA binding alters the structural properties of the DNA and enhances the binding of RNA polymerase. Moreover, a statistical analysis of the specificity of binding will be carried out by counting the number of specific vs. non-specific complexes for large numbers of molecules. A number of different salt and protein concentration conditions are assayed to increase the ratio of specific over non-specific complexation. Purification of RNA polymerase from *S. aureus* is straight forward, consisting of precipitation nucleic acid and bound proteins with PEI, ammonium sulfate precipitation, ion exchange chromatography and gel filtration chromatography.

Identification of Inhibitors of SarA Function

The present invention is based upon the knowledge that pleiotropically-acting regulatory factors are highly attractive targets for novel anti-staphylococcal therapies. Selecting inhbitors that interfere with SarA function which in turn affects the interaction of SarA and agr is particularly appealing, because one can inhibit both SarA and agr gene products at the same time. The design of effective inhibitors of the SarA-mediated activation of agr gene expression requires a detailed understanding of the mechanism of SarA regulation.

Any molecule that interferes with the SarA function involved in the expression of virulence factors are operable as inhibitors in the present invention. For example, molecules that would inactivate SarA, such as changing its structure or chemical conformation, resulting in its inability to bind to the agr locus is intended to be encompassed by the present disclosure. Particularly useful molecules in the present invention are inhibitors that bind to any one of the binding sites of SarA on the agr locus or several of these binding sites. The binding of these inhibitors to SarA's binding sites prevents the binding of SarA, thus preventing SarA from mediating virulence factor expression.

The present invention is directed to the development, synthesis and identification of inhibitors of virulence gene expression in *S. aureus*. One reasonable approach to this is to inhibit SarA-DNA interactions. However, another potentially potent point of inhibition is dimerization of the protein itself. If SarA cannot dimerize, it cannot activate agr gene expression. Therefore, it is important to identify the amino acid residues that are important for SarA activity, both DNA binding and dimerization. To accomplish this goal, the standard approaches of mutagenesis and subsequent activity assays are applied. Utilizing the 3-dimensional structure of the protein, specific amino acids for mutagenesis are chosen. Mutants are screened for activity in *S. aureus*. Additionally, the GST-SarA fusion protein used by Chien and Cheung (1998) in pGEX-4T-1 (Promega) was constructed to provide a possible explanation for disparate results as compared to those of the present invention.

Mutants of SarA and the SarA-DNA complex are designed. Two basic classes of mutants are important: 1) those that specifically disrupt DNA binding, and 2) those that affect dimerization. Residues K21, K23, K27, K28 (amino acid/position number) are targeted first as they line the basic region hole. Initially each of these residues are changed to alanine. However, alternative changes may be appropriate after completion of the analysis of the alanine substitutions. Mutants that will likely disrupt the subunit interactions are focused on F10, L12 and L13, all hydrophobic residues at the N-terminal end of helix 1 that is abutted against helix 5. For the mutagenesis, synthetic oligonucleotides are generated that incorporate the desired changes. These will be utilized in the Sculptor mutagenesis protocol according to the manufacturer's instructions (Amersham). The mutants are confirmed by sequence analysis.

The sarA mutant alleles to be tested in *S. aureus* are subcloned into pCL84 for integration into the chromosome of CYL316 (see above). Integrants are confirmed by lipase assay and by Southern blot with a geh probe. After confirmation, each sarA mutant is introduced into the PC1839 sar mutant (Table II) by Φ11-mediated transduction as described above. The activity of each mutant is assessed by northern blot using probes specific for RNAII and RNAIII (Gillaspy et al., 1995) and by analysis of an RNAIII-dependent target gene, hla. Expression of hla is assessed by northern blot, quantitative hemolysin assay and by western blot using rabbit α-toxin antisera.

Hippel (1989). The percentage of active SarA in the purified preparation is checked by stoichiometric DNA binding using EMSA with the A1/A2 DNA, as described above. This analysis addresses the fidelity of the protein in the purified sample.

For DNA-binding analysis, EMSA with synthetic oligonucleotide DNA targets, (e.g., A1/A2 from FIG. 3; Rechtin et al, 1999) is used. For these experiments, limiting $^{32}$P-labeled DNA is mixed with serially-diluted SarA and is resolved by native gel electrophoresis. Quantitation is accomplished by phosphorimaging of the unbound DNA in dried gels. The percent DNA bound is calculated, binding isotherms are generated and fit using BIOEQS and Origin. Under these conditions the $K_D$ equals the concentration of protein required to bind 50% of the input DNA (Hurlburt and Yanofsky, 1990).

TABLE II

Strains and plasmids

| Strain/plasmid | Description | Source (reference) |
| --- | --- | --- |
| RN6390 | 8325-4 laboratory strain | Richard Novick (Balaban and Novick, 1995) |
| PC1839 | 8325-4 sarA mutant (Kan$^r$) | Simon Foster (Chan and Foster, 1998) |
| ALC136 | 8325-4 sarA mutant (Em$^r$) | Ambrose Cheung (Bayer et al., 1996) |
| WA400 | 8325-4 RNAlll (hld) mutant (Cm$^r$) | Steffan Arvidson (Janzon and Arvidson 1990) |
| RN6911 | 8325-4 agr-null mutant (Tet$^r$) | Richard Novick (Novick et al., 1993) |
| UAMS-173 | 8325-4 sar/agr mutant (Erm$^r$/Tet$^r$) | Mark Smeltzer (Blevins et al., 1999) |
| UAMS-1 | Clinical isolate (osteomyelitis) | Mark Smeltzer (Gillaspy et al., 1995) |
| UAMS-4 | UAMS-1 agr mutant (Erm$^r$) | Mark Smeltzer (Gillaspy et al., 1995) |
| UAMS-6911 | UAMS-1 agr-null mutant (Tet$^r$) | Mark Smeltzer (Gillaspy et al., 1997) |
| UAMS-929 | UAMS-1 sar mutant (Kan$^r$) | Mark Smeltzer (unpublished) |
| UAMS-930 | UAMS-1 sar/agr mutant (Kan$^r$/Tet$^r$) | Mark Smeltzer (unpublished) |
| DB | Clinical isolate (blood) | Ambrose Cheung (Cheung et al., 1992) |
| UAMS-931 | DB sar mutant (Kan$^r$) | Mark Smeltzer (unpublished) |
| UAMS-932 | DB agr mutant (Tet$^r$) | Mark Smeltzer (unpublished) |
| UAMS-933 | DB sar/agr mutant (Kan$^r$/Tet$^r$) | Mark Smeltzer (unpublished) |
| CYL316 | RN4220 (pYL112)19) | Chia Lee (Lee et al., 1991) |
| pCL84 | L54a (geh) integration vector (Tet$^r$ when integrated in *S. aureus*) | Chia Lee (Lee et al., 1991) |

With the advantage of designing the mutants based on the structure of SarA, important amino acid residues are identified readily using this approach. Different mutants in specific regions of SarA may have dramatically different activities and help identify the residues critical for function.

Mutant proteins that result in aberrant regulation of the P3 promoter arise from changes in DNA-binding, activation, or dimerization. To distinguish between these possibilities, the mutant proteins in *E. coli* are expressed, purified and tested for DNA binding and dimerization using assays described above (EMSA, cross-linking, x-ray crystallography and AFM).

The primers designed for cloning the wild type SarA coding region and PCR to amplify the mutant alleles are used and cloned into T7 expression vector pET9a. The construct is checked by sequencing. The purification protocol is developed is used to generate large quantities of pure SarA for biochemical analysis (Rechtin et al, 1999). This procedure is easy for two reasons: 1) both naturally occurring alleles of SarA (DB and RN6390) behave identically in the purification procedure, 2) all of the many mutants of other proteins that the PI has dealt with previously (mostly *E. coli* trip repressor) behaved essentially like the wild type in purification. The concentration of the purified protein is determined spectrophotometrically at 280 nm using an extinction coefficients that are calculated from the mutant amino acid sequence using the method of Gill and von For dimerization analysis, chemical crosslinking as described above is used. Various concentrations of wild type SarA and mutant SarA is exposed to agents shown to be effective as described above (BS$^3$ or DSS). The samples are quenched and resolved by SDS-PAGE. If the protein is less able to dimerize, relative to the wild type, a higher concentration of protein is required to achieve 50% dimer in this assay. This assay reflects the relative ability of the mutant to dimerize, rather than a $K_D$ for the monomer-dimer equilibrium. Mutant proteins are be tested by dynamic light scattering as described above.

Blocking a cis-acting binding site for SarA with a small molecule inhibits SarA-mediated gene activation. In the present invention, the binding sites are those identified already herein and in Rechtin et al, (1999) and those that are cis to the P3 promoter. Among the small molecules that have the desired properties, peptide nucleic acid (PNA) and hairpin polyamides (HP) have received the most attention and show the most promise as pharmacological agents (e.g., Gottesfeld et al., 1997; Corey 1997; White et al., 1998; Good and Nielsen, 1998; Dickinson et al., 1998). Based on the analysis of the cis regulatory sites discussed above, appropriate test PNA and HP molecules for use as antistaphylococcal agents have been designed, synthesized and tested.

Figure 14:
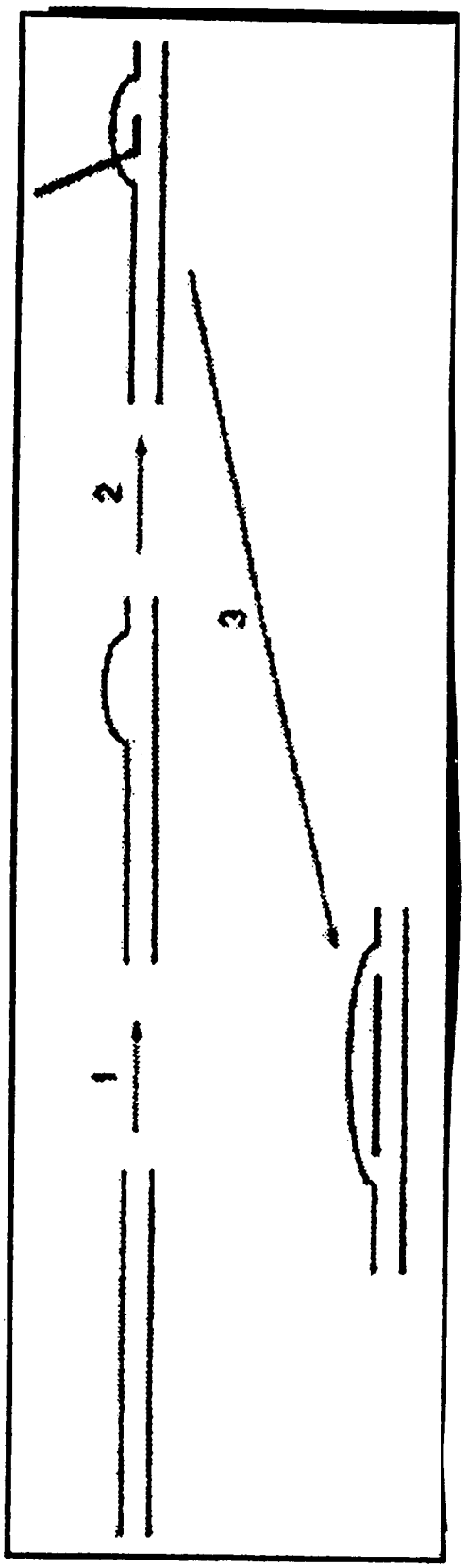
FIG. 14 depicts a PNA invading duplex DNA to form a ternary PNA-DNA complex.

PNA utilizes Watson-Crick base pairing for specificity. The advantages of PNA-like molecules are many. First, they are not found in nature and thus are more stable than DNA or RNA. Additionally, they do no have a negatively charged backbone which makes them bind to DNA or RNA more stably than DNA or RNA would bind. The DNA-PNA heteroduplex is much more stable that the DNA-DNA homoduplex because of the lack of negative charge on the PNA backbone and electrostatic repulsion. As a result PNA can displace a strand of duplex DNA as shown in FIG. 14. The resultant trimeric complex does not resemble a binding site for proteins. In fact, PNA has been successfully used to inhibit gene expression when designed to interfere with RNA polymerase and/or transcription factor binding (Hanvey et al., 1992; Knudsen and Nielsen, 1997; Boffa et al. 1997; Lee et al., 1998). In addition, appropriately designed PNA molecules also inhibit gene expression in bacteria and bacterial cell growth (Good and Nielsen, 1998a and 1998b, respectively). The main problem with using PNA to inhibit cell growth is low membrane permeability (Wittung et al., 1995; Good and Nielsen, 1998a and 1998b). Nevertheless, considerable effort is underway in many academic and pharmaceutical laboratories to overcome this limitation via chimeric PNA molecules (personal communication). For example, PNA-peptide chimeric molecules show promise in this area (personal communication). The peptide is utilized to facilitate endocytosis and is digested by intracellular proteases. This has the added feature of concentrating the PNA inside cells. Unlike antisense strategies with RNA or DNA, PNA is not degraded by cellular enzymes.

As discussed above, PNA molecules alone have one documented drawback, they do not cross membranes well. Currently, a tremendous amount of effort is being spent in academic and industrial settings to derive "carriers" for PNA. For example, one research group has published increased membrane passage by PNA-peptide conjugates (Hamilton et al., 1999) and another group has published a synthesis of PNA-peptide conjugates (Goodwin et al. 1998). These conjugates provide a carrier for membrane passage that is applicable to the SarA function inhibitors of the present invention. Furthermore, a world leading PNA research group has recently published a PNA conjugate that is readily taken up by cells (Ljungstrom et al., 1999). Further, another group found that polyarginine (9-mer) was very useful as a "cellular pass" and increases the rate of uptake of many drugs significantly (Service, 2000). Peptides are the simplest conjugates to prepare because PNAs are synthesized by the same chemistry methods used to synthesize peptides. All of these efforts are aimed at human diseases and PNA uptake by human cells and applicable in treating Staphylococcus infections. Because the Staphylococci are taking up peptides and oligonucleotides as their colony is growing, coupling PNA and other inhibitors to peptides enhances the uptake of PNA by the bacteria.

HP molecules are polymers of N-methylimidazole and N-methylpyrrole amino acids that bind specifically in the minor groove of duplex DNA (Wemmer and Dervan, 1997). In recent years HPs have been developed that can be designed to target any DNA sequence (White et al., 1998). Like PNAs, HPs protect the DNA from DNase I digestion and interrupt normal DNA binding by proteins. Both Pol II and Pol III gene expression has been shown to inhibited by specific HPs (Gottesfeld et al., 1997; Dickinson et al., 1998). HPs currently have an apparent advantage over PNAs, namely that they are readily assimilated into cells (Gottesfeld et al., 1997; Dickinson et al., 1998). Like PNA, HP molecules are not degraded enzymatically.

In the present invention, PNA and HP molecules are synthesized that are designed to interrupt SarA-agr interactions. Appropriate molecules are selected by in vitro tests first and then as inhibitors of exoprotein expression. Molecules that are found to be effective in these tests are selected for testing in animal models of staphylococcal disease.

For PNA synthesis, standard procedures were followed (Goodwin et al., 1998). Briefly, the F-moc protected monomers for PNA synthesis are purchased from PE Biosystems (formerly Perceptive Biosystems). Disposable polypropylene chromatography columns are filled with polyethylene glycol-polystyrene resin. The scale of the synthesis is dependent on the amount of resin utilized. Following resin washing successive cycles of monomer coupling, capping, and deprotection, the PNA is released from the resin by treatment with trifluoroacetic acid. Purification of PNA molecules is by reverse phase HPLC and the fidelity of the synthesis is checked by MALDI-TOF mass spectrometry. Currently, a standard PNA molecule is synthesized in one day, purified in the second day and analyzed by mass spectrometry on the third day. With this rapid turn-around, a reasonably large number of PNAs for inhibition of SarA-agr interactions are screened.

A simple solid-phase synthesis of HP molecules has been reported (Baird and Dervan, 1996). The present approach is to test the sites of inhibitor binding with PNA molecules first, and those PNAs that are effective acted as a target for subsequent HP synthesis. For HP molecules only two monomers are required, each of which requires a 4–5 step synthesis. These steps are straightforward, efficient and generate gram-quantities of highly purified material after column chromatography (Baird and Dervan, 1996). The Boc-Py-OBt ester and Boc-Im acid monomers are prepared first. Solid-phase synthesis of the HP molecules are performed as described by Baird and Dervan (1996). The details of the synthesis are similar to standard Boc-peptide synthesis. The HP molecules are released from the solid support and purified by reverse phase HPLC. The fidelity of the synthesis is checked by MALDI-TOF mass spectrometry.

The first tests of potential inhibitors are made using EMSA. Briefly, $^{32}$P-labeled DNA fragments that correspond to the PNA or HP molecules are used as the targets. For example, a PNA designed to bind to the A1 site (FIG. 3) is tested using the A1/A2 DNA fragment. The concentration of SarA required to bind 50% of the DNA fragment is determined empirically. To determine the degree of inhibition, a mixture of SarA and $^{32}$P-labeled DNA that gives 50% free DNA and 50% bound DNA (called 100% in this assay) is titrated with the PNA molecule. The concentration of PNA that reduces the SarA-DNA complex by 50% is the $IC_{50}$ value. Using this simple, but effective testing procedure, the PNA or HP design is varied with regard to the sequence targeted and the length of PNA or HP molecules. Iinhibitory PNA and HP molecules are tested against other binding sites for SarA, because the most effective inhibitors are those that can interupt SarA-DNA interactions at multiple sites.

PNA and HP molecules that are effective in the EMSA assay are tested for inhibition of RNAIII expression using *S. aureus* strains RN6390, DB and UAMS-1. RNAIII expression is assessed by northern blot as previously described (see above). The expression of RNAIII and/or SarA-dependent target genes including α-toxin, lipase, and protein A also is tested. Briefly, strains are grown in tryptic soy broth to early log phase. Putative inhibitors are added at various concentrations and the cultures allowed to grow for various periods. Samples taken from midexponential and post-exponential phase cultures are processed by centrifugation, with the supernatant used for analysis of exoproteins (e.g. α-toxin and lipase) and the cell pellet used to isolate RNA and for the analysis of surface proteins (e.g. protein A). Production of α-toxin is assessed by quantitative hemolysin assay and by western blot (see above). Lipase production is determined using a quantitative spectrophotometric assay employing tributyrin as substrate (Smeltzer et al., 1992). Protein A production is be assessed by northern blot using a spa probe and by western blot using non-immune rabbit serum. Inhibitors of interest results in reduced production of RNAIII, reduced production of α-toxin and lipase, and increased production of protein A. To confirm the specificity of the inhibitor, parallel cultures of WA400 (RNAIII⁻) and derivatives generated by transducing the WA400 RNAIII mutation into DB and UAMS-1 also are included.

Figure 15:
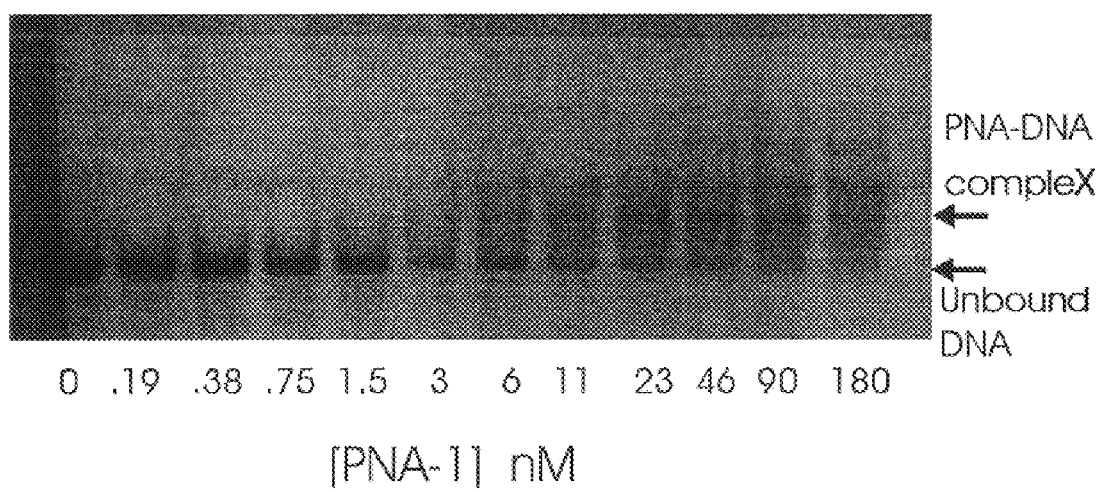
FIG. 15 depicts the results of a binding experiment between the SarA binding site A1/A2 and a PNA molecule.

A prototype PNA inhibitor of SarA-agr binding is constructed and tested. The is molecule has the sequence gly-TTTCTTAACTA-lys (SEQ ID NO:5), where the gly is a glycine amino acid on the amino terminus and the lys is a lysine amino acid on the C-terminus. These terminal amino acids are thought to increase the solubility of the PNA and perhaps increase the ability of the molecule to traverse the cell membrane. The TTTCTTAACTA (SEQ ID NO:6) sequence is identical to the 3' end of the A1 half site, and should hybridize to the lower strand in FIG. 3. The PNA (PNA-1) was synthesized according to Goodwin et al. (1998) and purified by HPLC. The fidelity of the synthesis and confirmation of the structure of PNA-1 was accomplished by mass spectrometry. The results show that the molecule binds to an oligonucleotide that includes the A1/A2 boxes (the A1/A2 oligo from FIG. 3.) 20 nM A1/A2 was radiolabeled with $^{32}$P and incubated with varying concentrations of PNA-1. The complexes were resolved by native gel electrophoresis and detected by phosphorimaging. FIG. 15 shows the results of this representative experiment. The duplex DNA target and the heteroduplex of PNA-1-DNA are labeled. It is clear from this experiment that 1) the affinity of PNA-1 for the A1/A2 oligonucleotide is very high, and 2) that nearly all, if not all, of PNA-1 is active in this assay.

Figure 16:
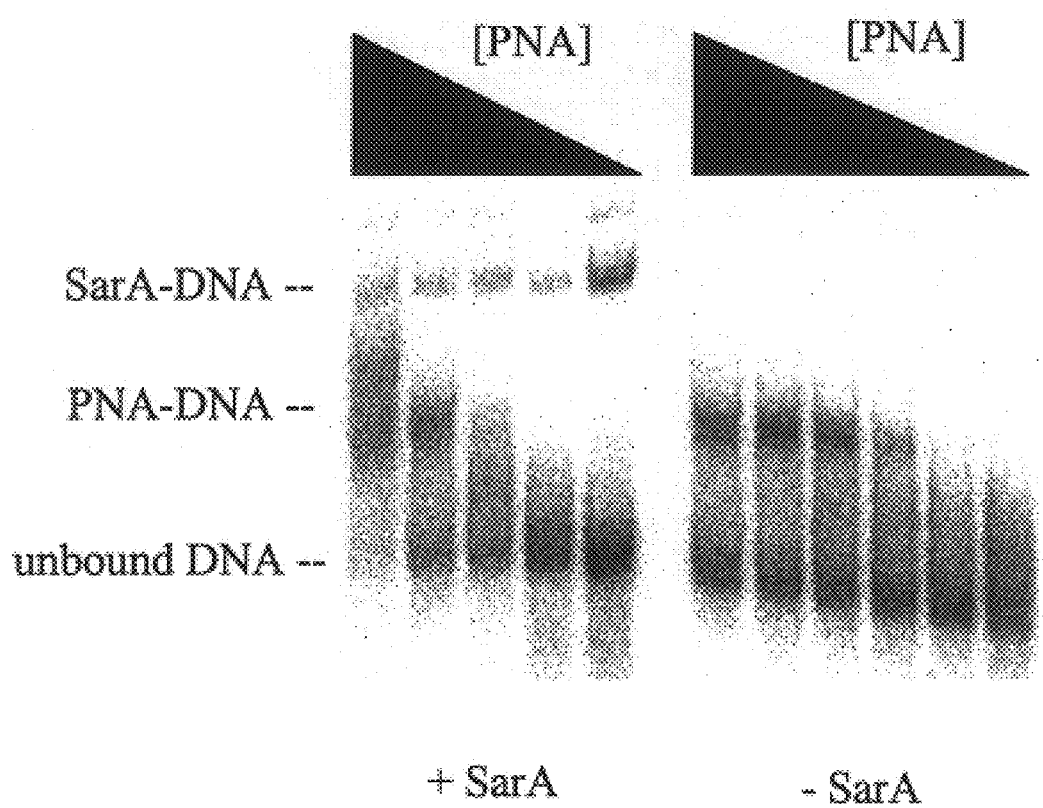
FIG. 16 depicts the results of a binding experiment between the SarA binding site A1/A2 and a PNA molecule with and without the addition of SarA.

The ability of PNA molecules to compete for SarA binding to the A1 site is shown in FIG. 16. Radiolabelled dsDNA (10 nM) corresponding to the A1/A2 binding site is mixed with either varying concentrations of PNA (right panel) or varying concentrations of PNA (0.750 pM, 7.5 nM, 75 nM and 750 nM) and a fixed concentration of pure SarA (10 nM) is added to the solution after the A1/A2 binding site (left panel) and the PNA has been incubated together overnight in EMSA buffer. These experiments are performed according to the methods disclosed in Rectin et al.,1999. The samples were analyzed by standard EMSA and phosphorimaging. It is clear that the PNA molecule is able to outcompete SarA for binding to the DNA, and forms a protein-DNA complex. However, increasing concentrations of PNA are able to compete with SarA for binding the DNA and the SarA-DNA complex is diminished. The PNA molecule used in this experiment is an 18-mer: gly-TCCAATTTTCTTAACTA-lys (SEQ ID NO:7).

To determine the minimum length PNA molecule required in the present invention to inhibit SarA function, the 11-mer, gly-TTTCTTAACTA-lys (PNA) (SEQ ID NO:5), was incubated with a mixture of SarA and radiolabeled ds A1/A2 DNA, as disclosed above and in Recin et al., 1999. The SarA and the A1/A2 DNA formed a complex, and the addition of the 11-mer did not change this complex. However, when the 18-mer (PNA) described above was added to the complexed SarA and radiolabeled ds A1/A2 DNA, the complex changed from the SarA-DNA complex to the PNA-DNA complex, suggesting that the latter complex was more stable than the former. This result also suggests that the minimum length of a PNA molecule must be greater than 11 derived nucleotides to compete out the binding of SarA to its binding site, and an 18-mer was of a sufficient length to displace the SarA from the DNA. The present invention provides a method to determine the minimum and/or optimum length of the SarA function inhibitor that is operable in the present invention.

Antisense molecules (oligonucleotide analogs) to the sar gene or to the SarA binding sites on the agr locus are also inhibitors of the SarA function involved in the expression of virulence factors in staphylococcal infections. Most commonly, these inhibitors are relatively small RNA or DNA molecules because they can be designed to be highly specific. In general, so-called "antisense" molecules have a sequence which is complementary to a portion of the mRNA.

As indicated, the antisense molecules can have a variety of chemical constitutions, so long as they retain the ability specifically to bind at the indicated control elements. Thus, especially preferred molecules are oligonucleotide analogs -DNA, RNA, protein nucleic acids (PNAs) and phosphothiolate oligonucleotides. The oligonucleotides of the present invention are based, for example, upon ribonucleotide or deoxyribonucleotide monomers linked by phosphodiester bonds, or by analogues linked by methyl phosphonate, phosphorothioate, or other bonds. These are engineered using standard synthetic techniques to very specifically bind the targeted control region(s). While these molecules may also be large, they are preferably relatively small, i.e., corresponding to less than about 50 nucleotides, more preferably less than about 25 nucleotides. Such oligonucleotides may be prepared by methods well-known in the art, for instance using commercially available machines and reagents available from Perkin-Elmer/Applied Biosystems (Foster City, Calif.).

Phosphodiester-linked oligonucleotides are particularly susceptible to the action of nucleases in serum or inside cells, and therefore in a preferred embodiment the oligonucleotides of the present invention are phosphorothioate or methyl phosphonate-linked analogues, which have been shown to be nuclease-resistant Stein et al. (1988). Persons knowledgeable in this field will be able to select other linkages for use in the present invention.

To select the preferred length for an antisense oligonucleotide, a balance must be struck to gain the most favorable characteristics. Shorter oligonucleotides 10–15 bases in length readily enter cells, but have lower gene specificity. In contrast, longer oligonucleotides of 20–30 bases offer superior gene specificity, but show decreased kinetics of uptake into cells. See Stein et al. (1988). In a preferred embodiment, this invention contemplates using oligonucleotides approximately 14 to 25 nucleotides long.

PNAs, HPs and antisense molecules are delivered in a variety of ways. They are synthesized and delivered as a typical pharmaceutical, usually parenterally. They are formulated as detailed below, but one preferred formulation involves encapsulation/association with cationic liposomes. They can be modified with a targeting sequence or optionally linked to a polyamine, such a polylysine. See Bachmann et al., (1998) for one approach to delivering antisense molecules using a targeting sequence. Alternatively, antisense molecules are delivered using gene therapy methods, detailed below. Using gene therapy vectors, single, or multiple tandem copies of antisense molecules can be used.

Administration of PNAs, HPs, and antisense oligonucleotides to a subject are effected orally or by subcutaneous, intramuscular, intraperitoneal, or intravenous injection. Pharmaceutical compositions of the present invention, however, are advantageously administered in the form of injectable compositions. A typical composition for such purpose comprises a pharmaceutically acceptable solvent or diluent and other suitable, physiologic compounds. For instance, the composition may contain oligonucleotide and about 10 mg of human serum albumin per milliliter of a phosphate buffer containing NaCl.

As much as 700 milligrams of antisense oligodeoxynucleotide has been administered intravenously to a patient over a course of 10 days (i.e., 0.05 mg/kg/hour) without signs of toxicity. Sterling (1992).

All of the patent documents and publications cited herein are hereby incorporated by reference in their entirety.

LITERATURE CITED

Abdelnour, A., et al. (1993) Infect. Immun. 61, 3879–3885.
Aggarwal, A., et al. (1988) Science 242, 899–907.
Aggarwal, A. (1990) Methods: A Companion to Methods in Enzymology 1, 83–90.
Ansari, A. Z., et al. (1995) Nature 374, 371–375.
Ansari, A. Z., et al. (1992) Nature 355, 87–89.
Aronson, B. D., et al. (1989) J. Bact. 171, 5503–5511.
Bachmann et al., J. Mol. Med. 76:126–32 (1998)
Baird, E. E. and Dervan, P. B. (1996) J. American Chemical Assoc. 118, 6141–6146.
Baker, E. N. (1995) In Gregory, R. B. (ed.), Protein-Solvent Interactions, Dekker Inc. New York, pp. 143–189.
Balaban, N., et al. (1998) Science 280, 438–440.
Bayer, M. G., et al. (1996) J. Bact. 178, 4563–4570.
Blevins, J., et al. (1999) Transcriptional regulation of the Staphylococcus aureus collagen adhesin gene (cna) by the staphylococcal accessory regulator (sar). submitted to Molecular Microbiolgy.
Boffa, L. C., et al. (1997) Oncology Research 9, 41–51.
Booth, M. C., et al. (1995) Invest. Ophthal. 36, 1828–1836.
Booth, M. C., et al. (1997) Infect. Immun. 65, 1550–1556.
Brunger, A. T.(1992) Nature 355, 472–474.
Bustamante, C. and Rivetti, C. (1996) Ann. Rev. Biophys. Biomol. Struct. 25, 395–429.
Chan, P. F. and Foster, S. J. (1998) J. Bact. 180: 6232–6241.
Cheung, A. L., et al. (1992) Proc. Natl. Acad. Sci. USA 89: 6462–6466.
Cheung, A. L. and Projan, S. J. (1994) J. Bact. 176: 4168–4172.
Cheung, A. L., et al. (1994a) Infect. Immun. 62, 1719-17–25.
Cheung, A. L., et al. (1994b) J. Clin. Invest. 94, 1815–1822.
Cheung, A. L., et al. (1997) J. Bact. 179, 3963–3971.
Chien, Y-t., and Cheung, A. L. (1998) J. Biol. Chem. 273, 2645–2652.
Corey, D. R. (1996) TIBTECH 15, 224–229.
Czernik, P. J., et al. (1996) J. Biol. Chem. 271, 9141–9149.
Deora, R. and Misra, T. K. (1996) J. Biological Chemistry 271, 21828–21834.
Devereux, J., et al. (1984) Nucl. Acid. Res. 12: 387–395.
Dickinson, A. G., et al. (1968) J. Bact. 95,418–425.
Dickinson, L. A., et al. (1998) PNAS USA 95 12890–12895.
Drenth, J. (1994) Principles of Protein X-ray Crystallography. Springer-Verlag Inc., New York, pp. 129–200.
Fernando, T. and C. Royer (1992) Biochemistry 31, 3429–3441.
Fluckiger, U., et al. (1998) Infection and Immunity 66, 2871–2878.
Frey, M. (1993) In Westhof, E. (ed.), Water and Biological Macromolecules. CRC Press, Inc., Boca Raton, pp. 98–147.
Furey, W. and Swaminathan, S. (1997) Meths Enzymol. 277, 590–620.
Gill, S. C. von Hippel, P. H. (1989) Anal. Bioch. 182(2), 319–26.
Gillaspy, A. F., et al. (1997) Infect. Immun. 65, 1536–1540.
Gillaspy, A. F., et al. (1998) Infect. Immun. 66, 3170–3178.
Gillaspy, A. F., et al. (1995) Infect. Immun. 63, 3373–3380.
Good, L. and Nielsen, P. E. (1998) Nature Biotechnology 16, 355–358.
Good, L. and Nielsen, P. E. (1998) P.N.A.S. USA 95, 2073–20876.
Goodwin, T. E., et al. (1998) Bioorganic and Medicinal Chemistry Letters 8, 2231–2234.
Gottesfeld, J. M., et al. (1997) Nature 387, 202–205.
Hamilton S E. et al. (1999) Chemistry & Biology. 6(6):343–51.
Hanvey, J. C., et al. (1992) Science 258, 1481–1485
Heinrichs, J. H., et al. (1996) J. Bact. 178, 418–423.
Hendrickson, W. A., et al. EMBO J. 9: 1665–1672 (1990).
Hurlburt, B. K. and Yanofsky, C. (1993) J. Biol. Chem. 268, 14794–14798.
Hurlburt, B. K. and Yanofsky, C. (1990) J. Biol. Chem. 265, 7853–7858.
Hurlburt, B. K. and Yanofsky, C. (1992) Nucl. Acids Res. 20, 337–341.
Jancarik, J. and Kim, S. H. (1991) J. Appl. Crystallogr. 24, 409–411.
Ji, G., et al. (1997) Science 276, 2027–2030.
Jones, T. A. (1985) Meths. Enzymol. B115, 157–171.
Jones, T. A., et al. (1991) Acta Crystallogr., A47, 110–119.
Jordan, S. R., et al. (1985) Science 230, 1381–1385.
Kelley, R. L., and Yanofsky, C. (1985) Proc. Natl. Acad. Sci. USA 82, 483–487.
Knudsen, H. and Nielsen, P. E. (1997) Anti-cancer Drug 8, 113–118
Lane, D., et al. (1992) Micr. Revs. 56, 509–528.
Laskowski, R. A., et al. (1993) J. Appl. Crystallogr., 26, 283–291.
Lavory, R. and Sklenar, H. (1988) J. Biomol. Struct. Dynam. 6, 63–91.
Lee, C. Y., et al. (1991) Gene 103,101–105.
Lee, R., et al. (1998) Biochemistry 37, 900–910.
LeMaster, D. M and Richards, F. M. (1985) Biochemistry 24, 7263–7268.
Ljungstrom, E., et al. (1999) Biochem. and Mol. Biol. 10, 965–972.
Mackintosh, S. G., et al. (1998) Mol. Micro. 27(6), 1119–1127.
Maleki, S. J., et al. (1997) Biochemistry, 36, 6762–6767.
Margeat E. et al. Biophysical Journal. 75(6):2712–20, December 1998
McPherson, A. (1990) Eur. J. Biochem. 189, 1–23.
Miller, J. H. (1972) Experiments in Molecular Genetics (Cold Spring Harbor Laboratory, Cold Spring Harbor, N.Y.).
Morfeldt, E., et al. (1988) Mol. Gen. Genet. 211:435–440.
Morfeldt, E., et al. (1996) Mol. Micro. 21, 1227–1237.
Nikiforov, T. T. and Jeong, S. (1999) Analytical Biochemistry 275, 248–253.
Novick, R. P., et al. (1993) EMBO J. 12, 3967–3975.
Novick, R. P., et al. (1995) Mol. Gen. Genet. 248: 446–458.
Otto,M., et al. (1998) FEBS Lett. 424, 89–94.
Peng, H. L., et al. (1988) J. Bact. 170: 4365–72.
Projan, S. J. and Novick, R. P. (1997) The Molecular Basis of Pathogenicity, in The Staphylocci in Human Disease. Crossley and Archer, (Eds.), Churchill Livingstone, NY.
Ray, C., et al. (1997) J. Bact. 163, 610–614.

Rechtin, T. C.; et al. (1999) *Molec. Micro.* 33:2, 307–316.
Recsei, P., et al. (1986) *Mol. Gen. Genet.* 202:58–61
Remington's Pharmaceutical Sciences: Drug Receptors and Receptor Theory, Mack Publishing Co., Easton, Pa. (1990).
Riggs, A. D., et al. (1970) *J. Mol. Biol.* 48, 67–83.
Royer, C. A., et al. (1990) *Anal. Biochem.* 191: 287–294.
Royer, C. A. & Beechem, J. M. (1992) *Meth. Enzym.* 210: 481–505.
Royer, C. A. (1993). *Anal. Bioch.* 210: 91–97.
Saravia-Otten, et al. (1997) *Infect. Immun.* 179, 5259–5263.
Schultz, S. C., et al. (1990) *J. Mol. Biol.* 213, 159–166.
Schumacher, M. A., et al. (1998) In press, *EMBO J.*
Schumacher, M. A., et al. (1994) *J. Mol. Biol.* 242, 302–305.
Schumacher, M. A., et al. (1996) *Nature Struct. Biol.* 3, 881–887.
Service, R. F. (2000) *Science* 288, 28b.
Sieradzki, K. and Tomasz, A. (1999) Microbial Drug Resistance 4, 159–168.
Smeltzer, M. S., et al. (1992) Applied and Environmental Microbiology 58, 2815–2819.
Smeltzer, M. S., et al. (1996) *J. Clin. Micro.* 34, 1364–1372.
Smeltzer, M. S., et al. (1997) *J. Clin. Micro.* 35, 2444–2449.
Smith et al., 1999:(1999) New England J. Medicine 340, 493–501
Stein et al., Phosphorothioate Oligodeoxynucleotide Analogues in *Olipodeoxynucleotides—Antisense Inhibitors of Gene Expression,* Cohen, Ed. McMillan Press, London (1988).
Sterling, *Genetic Engineering News* 12: 1, 28 (1992)
Straus, E. (1998) *Science* 280, 379.
Tenover, F. C., et al. (1998) *Clinical Micro.* 36, 1020–1027.
Terwilliger, T. C. and Eisenberg, D. (1983) Acta Crystallogr. A39, 813–817.
Tronrud, D. E., et al. (1987) *Acta Crystallogr.*, A43, 489–501.
Wemmer, D. E. and Dervan, P. B. (1997) Current Opinion in Structural Biology 7, 355–361.
White, S. R., et al. (1998) *Nature* 391, 468–471.
Wittung, P., et al. (1995) FEBS Letters 365, 27–29.
Zheleznova, E. E., et al. *Prot. Sci.* 6, 2465–2468 (1997).
Zukowski, M. M., et al. (1983) *Proc. Natl. Acad. Sci. USA* 80, 1101–1105.

We claim:

1. A method of identifying inhibitors of the binding of SarA involved in the expression of staphylococcal virulence genes to at least one SarA binding site comprising:
   a) contacting a candidate inhibitor with at least one SarA binding site of the agr locus in solution to allow the binding reaction to equilibrate for a sufficient period of time, wherein said SarA binding site of the agr locus as depicted in FIG. 3 is at least one nucleotide sequence selected from the group consisting of at least the nucleotide sequences in the A1 (SEQ ID NO:12) and A2 (SEQ ID NO:14) boxes, at least the nucleotide sequences in the B1 (SEQ ID NO:16) and B2 (SEQ ID NO:17) boxes and at least the nucleotide sequences in the C1 (SEQ ID NO:15) and C2 (SEQ ID NO:13) boxes;
   b) assessing the binding of said candidate inhibitor to said SarA binding site of the agr locus; and
   c) selecting said candidate inhibitor that binds to the agr locus.

2. The method of claim 1, wherein said assessment of binding of the inhibitor to said SarA binding site is performed by an electrophoretic mobility shift assay for fluorescence anisotropy.

3. The method of claim 1, wherein said candidate inhibitor interferes with SarA mediated activation of the agr locus.

4. The method of claim 3, wherein said candidate inhibitor interferes with the binding of SarA to at least a portion of the agr locus.

5. The method of claim 4, wherein said portion of the agr locus is composed of greater than about 70% A-T nucleotides.

6. The method of claim 5, wherein said portion of the agr locus is composed of between about 79–89% A-T nucleotides.

7. The method of claim 6, wherein said candidate inhibitor interferes with the binding of SarA to at least a portion of the agr locus depicted in FIG. 3 (SEQ ID NOS:10 and 11).

8. The method of claim 1, wherein said candidate inhibitor also interferes with the binding of SarA to the intervening nucleotide sequences between the A1 (SEQ ID NO:12) and A2 (SEQ ID NO:14) boxes when the inhibitor binds to the nucleotide sequence in the A1 (SEQ ID NO:12) and A2 (SEQ ID NO:14) boxes, to the intervening nucleotide sequences between the B1 (SEQ ID NO:16) and B2 (SEQ ID NO:17) boxes when the inhibitor binds to the nucleotide sequences in the B1 (SEQ ID NO:16) and B2 (SEQ ID NO:17) boxes or to the intervening nucleotide sequences between the C1 (SEQ ID NO:15) and C2 (SEQ ID NO:13) boxes when the inhibitor binds to the nucleotide sequences in the C1 (SEQ ID NO:15) and C2 (SEQ ID NO:13) boxes.

9. The method of claim 4, wherein said candidate inhibitor binds to at least a portion of the agr locus.

10. The method of claim 1, wherein said candidate inhibitor is selected from the group consisting of an oligonucleotide analog of the Sar A binding site of the agr locus and a hairpin polyamide.

11. The method of claim 10, wherein said oligonucleotide analog is selected from the group consisting of a peptide nucleic acid molecule, a DNA molecule, a RNA molecule and a phosphothiolate oligonucleotide.

12. The method of claim 1, further comprising the addition of SarA to the solution of step a) simultaneously with said contacting of said inhibitor and said SarA binding site, and assessing the binding affinity of said candidate inhibitor relative to the binding affinity of said SarA to said SarA binding site of the agr locus.

13. The method of claim 1, further comprising the addition of SarA to the solution of step a) sequentially after said contacting of said inhibitor and said SarA binding site, and assessing the binding affinity of said candidate inhibitor relative to the binding affinity of said SarA to said SarA binding site of the agr locus.

14. The method of claim 10, further comprising the addition of SarA to the solution of step a) simultaneously with said contacting of said inhibitor and said SarA binding site, and assessing the binding affinity of said candidate inhibitor relative to the binding affinity of said SarA to said SarA binding site of the agr locus.

15. The method of claim 10, further comprising the addition of SarA to the solution of step a) sequentially after said contacting of said inhibitor and said SarA binding site, and assessing the binding affinity of said candidate inhibitor relative to the binding affinity of said SarA to said SarA binding site of the agr locus.

16. The method of claim 11, further comprising the addition of SarA to the solution of step a) simultaneously with said contacting of said inhibitor and said SarA binding site, and assessing the binding affinity of said candidate inhibitor relative to the binding affinity of said SarA to said SarA binding site of the agr locus.

17. The method of claim 11, further comprising the addition of SarA to the solution of step a) sequentially after said contacting of said inhibitor and said SarA binding site, and assessing the binding affinity of said candidate inhibitor relative to the binding affinity of said SarA to said SarA binding site of the agr locus.

18. A method of identifying inhibitors of the binding of SarA involved in the expression of staphylococcal virulence genes to at least one SarA binding site comprising:
   a) contacting a candidate inhibitor that binds to at least a portion of the agr locus with at least one SarA binding site of the agr locus in solution to allow the binding reaction to equilibrate for a sufficient period of time, wherein said SarA binding site of the agr locus as depicted in FIG. 3 is at least one nucleotide sequence selected from the group consisting of at least the nucleotide sequences in the A1 (SEQ ID NO:12) and A2 (SEQ ID NO:14) boxes, at least the nucleotide sequences in the B1 (SEQ ID NO:16) and B2 (SEQ ID NO:17) boxes and at least the nucleotide sequences in the C1 (SEQ ID NO:15) and C2 (SEQ ID NO:13) boxes;

b) assessing the binding of said candidate inhibitor to said SarA binding site of the agr locus by adding SarA to the solution of step a) simultaneously with or sequentially with said contacting of said inhibitor and said SarA binding site, and assessing the binding affinity of said candidate inhibitor relative to the binding affinity of said SarA to said SarA binding site of the agr locus; and c) selecting said candidate inhibitor that binds to the agr locus as assessed relative to the binding affinity of SarA to the agr locus.

19. The method of claim 18, wherein said candidate inhibitor is selected from the group consisting of an oligonucleotide analog of the Sar A binding site of the agr locus and a hairpin polyamide.

20. The method of claim 19, wherein said oligonucleotide analog is selected from the group consisting of a peptide nucleic acid molecule, a DNA molecule, a RNA molecule and a phosphothiolate oligonucleotide.

21. The method of claim 18, wherein said assessment of binding of the inhibitor to said SarA binding site is performed by an electrophoretic mobility shift assay or fluorescence anisotropy.

22. The method of claim 18, wherein said portion of the agr locus is composed of greater than about 70% A-T nucleotides.

23. The method of claim 22, wherein said portion of the agr locus is composed of between about 79–89% A-T nucleotides.

24. The method of claim 18, wherein said candidate inhibitor interferes with the binding of SarA to at least a portion of the agr locus depicted in FIG. 3 (SEQ ID NOS:10 and 11).

25. The method of claim 18, wherein said candidate inhibitor also interferes with the binding of SarA to the intervening nucleotide sequences between the A1 (SEQ ID NO:12) and A2 (SEQ ID NO:14) boxes when the inhibitor binds to the nucleotide sequence in the A1 (SEQ ID NO:12) and A2 (SEQ ID NO:14) boxes, to the intervening nucleotide sequences between the B1 (SEQ ID NO:16) and B2 (SEQ ID NO:17) boxes when the inhibitor binds to the nucleotide sequences in the B1 (SEQ ID NO:16) and B2 (SEQ ID NO:17) boxes or to the intervening nucleotide sequences between the C1 (SEQ ID NO:15) and C2 (SEQ ID NO:13) boxes when the inhibitor binds to the nucleotide sequences in the C1 (SEQ ID NO:15) and C2 (SEQ ID NO:13) boxes.

* * * * *

```
                          SEQUENCE LISTING

<160> NUMBER OF SEQ ID NOS: 20

<210> SEQ ID NO 1
<211> LENGTH: 124
<212> TYPE: PRT
<213> ORGANISM: Staphylococcus aureus

<400> SEQUENCE: 1

Met Ala Ile Thr Lys Ile Asn Asp Cys Phe Glu Leu Leu Ser Met Val
1               5                   10                  15

Thr Tyr Ala Asp Lys Leu Lys Ser Leu Ile Lys Lys Glu Phe Ser Ile
            20                  25                  30

Ser Phe Glu Glu Phe Ala Val Leu Thr Tyr Ile Ser Glu Asn Lys Glu
        35                  40                  45

Lys Glu Tyr Tyr Leu Lys Asp Ile Ile Asn His Leu Asn Tyr Lys Gln
    50                  55                  60

Pro Gln Val Val Lys Ala Val Lys Ile Leu Ser Gln Glu Asp Tyr Phe
65                  70                  75                  80

Asp Lys Lys Arg Asn Glu His Asp Glu Arg Thr Val Leu Ile Leu Val
                85                  90                  95

Asn Ala Gln Gln Arg Lys Lys Ile Glu Ser Leu Leu Ser Arg Val Asn
            100                 105                 110

Lys Arg Ile Thr Glu Ala Asn Asn Glu Ile Glu Leu
        115                 120

<210> SEQ ID NO 2
<211> LENGTH: 124
<212> TYPE: PRT
<213> ORGANISM: Staphylococcus epidermidis

<400> SEQUENCE: 2

Met Ala Ile Ser Lys Ile Asn Asp Cys Phe Glu Leu Leu Ala Met Val
1               5                   10                  15

Thr Tyr Ala Asp Arg Leu Lys Gly Ile Ile Lys Lys Glu Phe Ser Ile
            20                  25                  30
```

Ser Phe Glu Glu Phe Ala Val Leu Thr Tyr Ile Ser Glu Asn Lys Glu
            35                  40                  45

Glu Glu Tyr Tyr Leu Lys Asp Ile Ile Asn His Leu Asn Tyr Lys Gln
 50                  55                  60

Pro Gln Val Val Lys Ala Val Lys Asn Leu Ser Gln Glu Asn Tyr Phe
65                  70                  75                  80

Asn Lys Lys Arg Asn Glu His Asp Glu Arg Thr Val Leu Ile Leu Val
                85                  90                  95

Asp Ser Lys Gln Arg Lys Lys Ile Asp Asp Leu Leu Lys Arg Val Asn
                100                 105                 110

Asn Arg Ile Thr Glu Ala Asn Asn Glu Asn Glu Val
                115                 120

<210> SEQ ID NO 3
<211> LENGTH: 32
<212> TYPE: DNA
<213> ORGANISM: Artificial Sequence
<220> FEATURE:
<221> NAME/KEY: misc_feature
<222> LOCATION: ()..()
<223> OTHER INFORMATION: primer incorporating the NdeI restriction
      enzyme site

<400> SEQUENCE: 3
gggaggtttt acatatggca attacaaaaa tc                              32

<210> SEQ ID NO 4
<211> LENGTH: 34
<212> TYPE: DNA
<213> ORGANISM: Artificial Sequence
<220> FEATURE:
<221> NAME/KEY: misc_feature
<222> LOCATION: ()..()
<223> OTHER INFORMATION: primer incorporating the BamHI restriction
      enzyme site

<400> SEQUENCE: 4
gtttaataga atggatcctc tatcaaactt cacc                            34

<210> SEQ ID NO 5
<211> LENGTH: 11
<212> TYPE: DNA
<213> ORGANISM: Staphylococcus aureus

<400> SEQUENCE: 5
tttcttaact a                                                     11

<210> SEQ ID NO 6
<211> LENGTH: 11
<212> TYPE: DNA
<213> ORGANISM: Staphylococcus aureus

<400> SEQUENCE: 6
tttcttaact a                                                     11

<210> SEQ ID NO 7
<211> LENGTH: 18
<212> TYPE: DNA
<213> ORGANISM: Staphylococcus aureus

<400> SEQUENCE: 7
tccaattttt cttaacta                                              18

-continued

<210> SEQ ID NO 8
<211> LENGTH: 117
<212> TYPE: DNA
<213> ORGANISM: Staphylococcus aureus

<400> SEQUENCE: 8 aattttctt aactagtcgt tttttattct taactgtaaa ttttttttatg ttaaaatatt    60 aaatacaaat tacatttaac agttaagtat ttatttccta cagttaggca atataat     117

<210> SEQ ID NO 9
<211> LENGTH: 117
<212> TYPE: DNA
<213> ORGANISM: Staphylococcus aureus

<400> SEQUENCE: 9
attatattgc ctaactgtag gaaataaata cttaactgtt aaatgtaatt tgtatttaat    60
attttaacat aaaaaaattt acagttaaga ataaaaaacg actagttaag aaaaatt     117

<210> SEQ ID NO 10
<211> LENGTH: 190
<212> TYPE: DNA
<213> ORGANISM: Staphylococcus aureus

<400> SEQUENCE: 10
cattaaaaca tgctaaaagc atttattttc caattttct taactagtcg ttttttattc    60
ttaactgtaa attttttat gttaaaatat taaatacaaa ttcatttaa cagttaagta   120 tttatttcct acagttaggc aatataatga taaaagattg tactaaatcg tataatgaca   180
ggatccccgg                                                         190

<210> SEQ ID NO 11
<211> LENGTH: 190
<212> TYPE: DNA
<213> ORGANISM: Staphylococcus aureus

<400> SEQUENCE: 11
ccggggatcc tgtcattata cgatttagta caatctttta tcattatatt gcctaactgt    60
aggaaataaa tacttaactg ttaaatgtaa tttgtattta atattttaac ataaaaaaat   120
ttacagttaa gaataaaaaa cgactagtta agaaaaattg gaaataaat gcttttagca   180 tgttttaagt                                                         190

<210> SEQ ID NO 12
<211> LENGTH: 18
<212> TYPE: DNA
<213> ORGANISM: Staphylococcus aureus

<400> SEQUENCE: 12
attttccaat ttttctta                                                 18

<210> SEQ ID NO 13
<211> LENGTH: 19
<212> TYPE: DNA
<213> ORGANISM: Staphylococcus aureus

<400> SEQUENCE: 13
ctgtcattat acgatttag                                                19

<210> SEQ ID NO 14
<211> LENGTH: 17
<212> TYPE: DNA

<213> ORGANISM: Staphylococcus aureus

<400> SEQUENCE: 14
taagaataaa aaacgac                                                        17

<210> SEQ ID NO 15
<211> LENGTH: 19
<212> TYPE: DNA
<213> ORGANISM: Staphylococcus aureus

<400> SEQUENCE: 15
caatataatg ataaaagat                                                      19

<210> SEQ ID NO 16
<211> LENGTH: 17
<212> TYPE: DNA
<213> ORGANISM: Staphylococcus aureus

<400> SEQUENCE: 16
ttaaatacaa attacat                                                        17

<210> SEQ ID NO 17
<211> LENGTH: 17
<212> TYPE: DNA
<213> ORGANISM: Staphylococcus aureus

<400> SEQUENCE: 17
gaaataaata cttaact                                                        17

<210> SEQ ID NO 18
<211> LENGTH: 12
<212> TYPE: DNA
<213> ORGANISM: Staphylococcus aureus

<400> SEQUENCE: 18
attataaaat wt                                                             12

<210> SEQ ID NO 19
<211> LENGTH: 124
<212> TYPE: PRT
<213> ORGANISM: Staphylococcus aureus

<400> SEQUENCE: 19

Met Ala Ile Thr Lys Ile Asn Asp Cys Phe Glu Leu Leu Ser Met Val
1               5                   10                  15

Thr Tyr Ala Asp Lys Leu Lys Ser Leu Ile Lys Lys Glu Phe Ser Ser
            20                  25                  30

Ile Ser Phe Glu Glu Phe Ala Val Leu Thr Tyr Ile Ser Glu Asn Lys
        35                  40                  45

Glu Lys Glu Tyr Tyr Leu Lys Asp Ile Ile Asn His Leu Asn Tyr Lys
    50                  55                  60

Gln Pro Gln Val Val Lys Ala Val Lys Ile Leu Ser Gln Glu Asp Tyr
65                  70                  75                  80

Asp Lys Lys Arg Asn Glu His Asp Glu Arg Thr Val Leu Ile Leu Val
                85                  90                  95

Asn Ala Gln Gln Arg Lys Lys Ile Glu Ser Leu Leu Ser Arg Val Asn
            100                 105                 110

Lys Arg Ile Thr Glu Ala Asn Asn Glu Ile Glu Leu
        115                 120

-continued

```
<210> SEQ ID NO 20
<211> LENGTH: 8
<212> TYPE: PRT
<213> ORGANISM: Staphylococcus aureus

<400> SEQUENCE: 20

Tyr Ser Thr Cys Asp Phe Ile Met
1               5
```